United States Patent [19]

Comai et al.

[11] Patent Number: 5,187,267
[45] Date of Patent: Feb. 16, 1993

[54] PLANT PROTEINS, PROMOTERS, CODING SEQUENCES AND USE

[75] Inventors: Luca Comai, Seattle, Wash.; Ann J. Koning, Davis, Calif.

[73] Assignee: Calgene, Inc., Davis, Calif.

[21] Appl. No.: 541,883

[22] Filed: Jun. 19, 1990

[51] Int. Cl.$^5$ .................... C07H 15/12; A01H 1/04; C12N 15/00; C12N 5/00

[52] U.S. Cl. ........................... 536/23.1; 800/205; 800/DIG. 40; 800/DIG. 44; 435/172.3; 435/240.4; 47/58; 935/35; 935/36; 935/67; 536/23.6; 536/24.1

[58] Field of Search ............ 536/27; 435/172.3, 240.4, 435/320.1; 800/205, DIG. 44; 935/35, 36, 67

[56] References Cited

FOREIGN PATENT DOCUMENTS 330479 8/1989 European Pat. Off. .

OTHER PUBLICATIONS

Smith et al. 1988. Nature 334:724–726.
Schoffl et al. 1986. Phil. Trans. R. Soc. Lond. 314B:453–468.
Schoffl et al. 1982. J. Mol. Appl. Genet. 1:301–314.
Nover et al. 1984. Eur. J. Biochem. 139(2):303–313.
Medford et al. 1989. The Plant Cell 1(4):403–413.
Key et al., "A Comparative Analysis of the Heat Shock Response In Crop Plants," Current Topics in Plant Biochemistry and Physiology (1983) 2:107–118.
Hackett and Lis, "Localization of the hsp83 Transcript Within a 3292 Nucleotide Sequence From the 63B Heat Shock Locus of D. melanogaster," Nucl. Acids Res. (1983) 11:7011–7030.
Czarnecka et al., "Comparative Analysis of Physical Stress Responses in Soybean Seedlings Using Cloned Heat Shock cDNAs," Plant Mol. Biol. (1984) 3:45–68.
Heikkila et al., "Induction of Heat Shock Protein Messenger RNA in Maize Mesocotyls by Water Stress, Abscisic Acid, and Wounding" Plant Physiol. (1984) 76:270–274.
Farrelly and Finkelstein, "Complete Sequence of the Heat Shock-inducible HSP90 Gene of Saccharomyces cerevisiae," J. Biol. Chem. (1984) 259:5745–5751.
Schoffl and Baumann, "Thermo-Induced Transcripts of a Soybean Heat Shock Gene After Transfer Into Sunflower Using a Ti Plasmid Vector," EMBO J. (1985) 4:1119–1124.
Lindquist, "The Heat-Shock Response," Ann. Rev. Biochem. (1986) 55:1151–1191.
Kulomaa et al., "Amino Acid Sequence of a Chicken Heat Shock Protein Derived from the Complementary DNA Nucleotide Sequence," Biochemistry (1986) 25:6244–6251.
Sargan et al., "hsp80, a Novel Heat Shock Inducible Protein of Chicken," Biochemistry (1986) 25:6252–6258.
Czarnecka et al., "DNA Sequence and Transcript Mapping of a Soybean Gene Encoding a Small Heat Shock Protein," Proc. Nat. Acad. Sci. (1985) 82:3726–3730.
Gurley et al., "Upstream Sequences Required for Efficient Expression of a Soybean Heat Shock Gene," Mol. Cell Biol. (1986) 6:559–565.
Rochester et al., "The Structure and Expression of Maize Genes Encoding the Major Heat Shock Protein, hsp70," EMBO J. (1986) 5:451–458.
Ananthan et al., "Abnormal Proteins Serve as Eukaryotic Stress Signals and Trigger the Activation of Heat Shock Genes," Science (1986) 232:522–524.
Lindquist and Craig, "The Heat-Shock Proteins," Ann. Rev. Genet. (1988) 22:631–677.

Primary Examiner—David T. Fox

[57] ABSTRACT

Novel nucleic acid sequences, constructs employing such sequences, transgenic plant cells and plants are provided employing sequences associated with tomato heat shock protein 80.5 ("hsp80"). Nucleic acid sequences obtainable from the use of hsp80 as a probe in other plant species are also disclosed. In particular, the 5' noncoding region of tomato hsp80 or other plant promoters obtainable therefrom, especially to provide differentially specific initiation of transcription of a desired nucleic acid sequence of interest. Also provided are putative sequences believed to represent Scaffold Attachment Regions (SAR) of the plant hsp80 gene.

20 Claims, 18 Drawing Sheets

```
      SduI
      SacI
      HgiJII                    SecI   [MfeI]             NlaIV
EcoRI HgiAI                     |      |                  |
|     |                         |      |                  |
1 GAATTCGAGCTCCCCCCCCAAAAGGCTGATCTGGTGAATAACCTGGTACAATTGCAAGGTCAGGAA  69
  IleArgAlaProProProGlnLysAlaAlaAspLeuValAlaAsnAsnLeuGlyThrIleAlaArgSerGlyT
  2                              12                      45              52                       69

PvuII
          NspBII
StyI      |
SecI      |
|         |
70 CCAAGGAGTTCATGGAAGCTCTTGCAGCTCTGGTGCTCAGCTGCTGATGTTAGCATGATTGGTCAATTCGGTGTAGGTT 138
   hrLysGluPheMETGluAlaLeuAlaAlaLeuAlaAlaGlyAlaAlaAspValSerMETIleGlyGlnPheGlyValGlyP
   71                                                   97
   71                                                   97

139 TCTTACTCTGCTTACTTGGTAGCTGAGAAGGTTGTTGTGACCACAAAGCACACAATGATGATGAGCAATATG 207
    heTyrSerAlaTyrLeuValAlaGluLysValValValThrThrLysHisAsnAspAspGluGlnTyrV
```

FIGURE 1A

```
                                            Cfr10I                              SecI                                   StyI
                                              |                                  |                                     SecI
                                                                                                                        |
208  TCTGGGAGTCTCAAGCCGGTGGCTCTCTTTCACTGTTACCAGGAGATACATCTGGTGAGAACCTTGGTAGGG                                                      276
     alTrpGluSerGlnAlaGlyGlySerPheThrValThrArgAspThrSerGlyGluAsnLeuGlyArgG
                        223                          245                          267
                                                                                    267

NlaIV
         KpnI
         HgiCI
          |||
277  GTACCAAGATGGTCCTTTATCTCAAGGAGGATCAGCTTGAATACCTTGAAGAACGTAGGCTCAAGGACC                                                        345
     lyThrLysMETValLeuTyrLeuLysGluAspGlnLeuGluTyrLeuGluGluArgArgLeuLysAspL
                       277                         281
                         279

BbvII
                                                                                  |
346  TGATTAAGAAGCACTCTGAGTTCATTAGCTATCCTATTTCTCTGTGGTTGAGAAGACCATAGAGAAGG                                                         414
     euIleLysLysHisSerGluPheIleSerTyrProIleSerLeuTrpValGluLysThrIleGluLysG
                                                                   406
```

FIGURE 1B

```
                        Ksp632I
                        |
415  AAATTTCTGATGATGAGGAGGAAGAGAAGATGAGGAGGAAAGGTAGAGGAGGTCGATGAGG       483
     luIleSerAspAspGluGluGluGluGluLysLeuLysGluGluGlyLysValGluValAspGluG
                                 431

Ksp632I
                |
484  AAAAGGAGAAGGAAGAGAAGAAAAAGAAGAAGTCAAAGAAGTTTCAATGAGTGGTCACTGGTGAACA       552
     luLysGluLysGluGluLysLeuLysLysLysLysValLysGluValSerAsnGluTrpSerLeuValAsnL
                    491

Tth111II  Ksp632I
                   |        |
553  AGCCAGAAGCCTATTTGGATGAGAATGAAAGCCAGAAGAGATCACAAAGGAAGAGTATGCTGCTTTCTACAAGA       621
     ysGlnLysProIleTrpMETArgLysProGluGluIleThrLysGluThrLysGluTyrAlaAlaPheTyrLysS
                     568              578                   593

MmeI
                    |
               Ksp632I
               |
622  GCTTGACTAATGATTGGGAAGAGCATCTTGCTCTGTGAAGGTCAGTTGGAGTTCA       690
     erLeuThrAsnAspTrpGluGluHisLeuAlaLeuValLysHisPheSerValGluGlyGlnLeuGluPheL
                       635                             662
```

FIGURE 1C

```
                    SduI
                    NlaIV
                    HgiJII
                    | | |
691 AGGCTGTCCTTTTGTTCCAAAAAGGGCTCCTCTTTGACCTTCTTTGACACAAAGAAGAAGCCCAACAACA    759
    ysAlaValLeuPheValProLysArgAlaProPheAspLeuPheAspThrLysLysLysProAsnAsnI
                              720
                              719
                              720

SspI
                                                    |
760 TCAAGTTGTATGTTCGCCGTGTGTTATCATGGATAACTGTGATGAGTTGATTCCTGAATATTTGAGCT    828
    leLysLeuTyrValArgArgValPheIleMETAspAsnCysAspGluLeuIleProGluTyrLeuSerP
                                                   820

GsuI
            |
829 TTGTGAAGGGTATTGTGGATTCTGAGGACCTTCCTCTCAACATTCCAGAGAGACATTGCAGCAGAACA    897
    heValLysGlyIleValAspSerGluAspLeuProLeuAsnIleSerArgGluThrLeuGlnGlnAsnL
                                858
```

FIGURE 1D

```
          XhoI
           -
898  AGATCCTAAAGGTTATTCGCAAGAATTGGTGAAGAAGTGTGTTGAGCTTTTCTTTGAAATTGCTGAGA   966
     ysIleLeuLysValIleArgLysAsnLeuValLysLysCysValGluLeuPheGluIleAlaGluA
      899
```

```
                                                                 HindIII
                                                                    -
967  ACAAGGAGGACTACAATAAGTTCTATGAGGCGTTCTCTAAAAAACCTCAAGCTTGGAATCCATGAGGATT   1035
     snLysGluAspTyrAsnLysPheTyrGluAlaPheSerLysLeuLysAsnLeuLysLeuGlyIleHisGluAspS
                                                          1015
```

```
                                                      NlaIV
                                                      KpnI
                                                 HgiCI
                                                  -  - -
1036 CTCAGAACACAGGGCAAAGTTTGCTGAACTGCTGAGGTACCACTCCACTAAGAGTGGTGATGAGATGACCA   1104
     erGlnAsnArgAlaLysPheAlaGluLeuLeuArgTyrHisSerThrLysSerGlyAspGluMETThrS
                                                 1070     1074
                                                      1072
```

```
1105 GCTTGAAGGACTATGTGACCAGAATGAAGGAGGCCAGAATGATATTTACTACATTACTGGTGAGAGCA   1173
     erLeuLysAspTyrValThrArgMETLysGluGlyGlnAsnAspIleTyrTyrIleThrGlyGluSerL
```

FIGURE 1E

```
                                                            GsuI    Eco57I
                                                             -       -
1174 AGAAGGCTGTTGAGAACTCTCCCTTCCTGGAGAAACTGAAGAAGAAGGGATATGAGGTGCTTTACATGG 1242
     ysLysAlaValGluAsnSerProPheLeuGluLeuLysLysLysGlyTyrGluValLeuTyrMETV
                                                           1222     1231

PvuII   HindIII
                                 NspBII  Eco57I
                                   -       -
1243 TTGATGCCATTGATGAGTATTCAATTGGTCAGCTGAAGGAATTTGAGGCAAAAAGCTTGTTTCTGCTA 1311
     alAspAlaIleAspGluTyrSerIleGlyGlnLeuGluPheGluGluLysLysLeuValSerAlaT
                         [MfeI]
                           -
                          1264                                 1297
                                                               1297

StyI   StuI
     SecI   HaeI   HindIII
      -      -       -
1312 CCAAGGAAGGCCTCAAGCTTGATGAGATTGAAGGAGATGAAGATGAGAGTGAAGATTGAAGGAGAAGT 1380
     hrLysGluGlyLeuLysLeuAspGluIleGluGlyAspGluAspGluSerGluAspLeuLysGluLysP
     1313   1322   1327
            1322

1381 TTGAGGGACTGTGTAAGGTGATGAGAAGGATGTGCTAGGAGACAAAGTTCATTGTTTCTGACC 1449
     heGluGlyLeuCysLysValMETLysAspValLeuGlyAspLysValGluLysValIleValSerAspA
```

FIGURE 1F

```
         Tth111I
         HindII
         - -
1450 GTGTTGTTGACTTCCCTGCTGTTTGGTCACTGGTGAGTATGGCTGGACTGCTAACATGGAGAGAATTA 1518
     rgValValAspSerProCysCysLeuValThrGlyGluTyrGlyTrpThrAlaAsnMETGluArgIleM
                                   1458
                                   1461

StyI
                                                                      SecI
                                                                      NcoI
                                                                      DsaI
                       NspI                                            BbvII
                       AflIII                                          -
                       - -
1519 TGAAGGCACAGGCACTTAGGACTCCAGCATGGCTGGATACATGTCTAGCAAGAAGACCATGGAGATCA 1587
     ETLysAlaGlnAlaLeuArgAspSerSerMETAlaGlyTyrMETSerSerLysLysThrMETGluIleA
              GsuI                    1559                         1579
              -                       1563                         1577
              1527                                                 1577
                                                                   1577
                                                                   1577

Ksp632I
                                 -
1588 ACCCAGAGAACTCCATCATGGATGAGCTAAGGAAGAGGGCTGATGCAGACAAGAATGACAAGTCTGTGA 1656
     snProGluAsnSerIleMETAspGluLeuArgLysArgAlaAspAlaAspLysAsnAspLysSerValL
                                 1615

FIGURE 1G
```

```
                    VspI                    NlaIV
                     |                        |
1864 AAGTTCATTAATGTTTTGATAGTTTTTATGGGTTCCTTTACTACTACTTTTATTCCCTAGTTTTTGCTTTTA 1932
                 1872                      1896

1933 TCCCATCAGAACAATATGTGAGGGTTTTAATGCCGTTCTTTTAGAATGGCAGTTCAATGTTAGGTTATA 2001

2002 ATTCTCTTTTTGTTTTGACATTCGTGGTTGATATAGTTTATTTTCTTGCCCAAAAAAAAAAAAAAAA 2070

NlaIV
                                                KpnI
                                            HgiCI
                                             | | |
2071 AAAAAAAAAAAAAAAAAAAAAAAAAAAAAAAAAAAAAAAAAAAGCTCCGGTACCC 2116
                                            2111
                                               2115
                                             2113
```

FIGURE 1I

```
GAATTCAATT TATTACTTTC TTTCAATAT  AAAAAGTTT  TATTTTTCC  GATCTTAAAC TAAAGATATA
TATATACTGA AATATTTTA  ATTGTGTGGT CTTAAACATA TCAAGTGGAA GTTAAAATTT AAAATTGATT
......                                      .                               ......

CATAAGAAAA ACATTCTTA  ATATTTTGAA ACTAATTAGA ACATTCTTTA TTTGTTTTTG TTAAAAAAAA

ATTAAAATAA TTTTATTATT ACTAAAAAAT TAGACGTTCC ATTTTGAGGC CAAGCTATCT TTAAAGGTAT
TGGGTCACCC GTATGTCCAA TTGCATATGA GAAAGTAAAA TAATTGAGCT TGTTTGTTGT TAGTACATGA
TTCATGTTTT GAAATATAAT TGGCTTGCAA TAACATGAAA AATATTTATA AGCAAAACAA TATTTGAAAA
AAAAGTTGA  ATAAAATTCA AGGATGATTT ATATATGTTC GAACAAATCA TATTCTTCCA TTGCTTGATA
ATTGCAATAA GATAATTTTG TGTATGATAT CAATAAAATTA TAGAGTATGT AATATAATA  AGATAATTTT
GCGTAAGATA CCGATAAATT ATAGAATATG TGAAGTCAAG GATGTTTGTA CATAAGCTAA TTGGATCATA
AGGTTTTGGT ATTTATATTT TTGCAGCAGA CATCTTATGC ATGCGACTTT GAAATTTATC CCATTACAAT
CTTAAGTAAT TTTTTAGTTC TACATTAGAA GAACGAAGTT GATCTTTCGT GAACATAGTG ACTTTCTGGT
ATGTTAAATC AAGACACATT ACACAACATT CTTTAGTAAA AAAAATTTCT CAACAGAGCT ATGATTATGC
GTAAATAATA CACTCTCTCC CTAACTTGAT TATTTTGAAA AGTGAAAGAA TAAAACAAAG TAAAAAATAC
TAAAACCAA  ATCAATTTTC ACAACGTCTC ACTCAATTTT TTCCACGATA TTGAAAAATA TTTTCATAGA
CGTATGCACC AAAGTATATG CAGAAATCAC ATATAGTCTT TTGTTTGAAC AATGAATCAA TAATTGACGG
TATATATTAA TATACATATA ACATCACATA TGGTTAAAAG CCTTTACAAT ACATATTAAT TACTTATAAT
TAGGATAAAT GGCAGCAACA TATATTTGAA ATATTGTTAA CACCTTCCTC CACTTCCACG TGGAAAGTGA
CTAAAATAAA TATAATTTTT TGAATATATC ATAATCAAGA GAAAATTATT TCAAACAAAG TCCATATCAT
ATAATAGTAG TTAGTTTCTT CACCTAACTA GATTTACTAT CTCTGTTAAA ATATTAATAA TTAATAAAAA
.....      .

AGTCATATAA AATAAATACT TATGCAAATT ATTGTATCTA AAGATTTTTT CTTTTCCACA AATATTTAAT
ACCTTGTGTA TATAGTTTTG TATTTAAGTT AAAATATGAT GTTATAAAAA AATGTATAAT GTTATAATAA
AATTCTCAAA TTAAGACTCG TAAGAGTTTT TAAGAGTTT  ATATGAAACA AAAAATAATT CTAGACATCC AAGGTGTTAC
```

FIGURE 2A

```
ATTAGAAAAT CTTGTCATTT TAATAATACA TTCATAACAT ATAGTATATT AATAAAAATA TTTATCTCAT
            ...         ......
AAAGATTAAC AATTAAAAAT AAATAATAAA ATTTAAAATA ATACAAATTT CAATTGACAT TAATAAAAAT
                      ......
AAACCAAAAT CCAAAAATAA AATTAAAAATTT ACCATCCATA TTTATGACAT TTTATCGTAT AAATACTTCT
                                   ...
AATTTAATAC ATTTCTATAG TTTTAATATT ATTATCAAAG GTTTGGAAAT TAAAATAAATA TTTTCAATCG
                                  ......
AATATTTCGA CTTCAAAATT TTAATAATCA AATAAATTGT GTGAAAATCC TTTTTTTGCT CAAAATAATT
TCTAAAACGG GTTATGATTG ATGAGAAAAC GTAAAAGTGT GATTAGAGCT TAATTAAAAT AGGCTCTCCA
            ...       ........   +++         +++++++++++   ++
TATCCAATTA TTAGAAAAAT TAAAAATAAT AAATAATAGC CCATAGAAGG ATCTAGAAAC CCTAAATAGG
 ******      **                               S
CTAGTATATA AAGTCGCTAA AAACTTCCCT TGATCCCTCC↧ C↧TTGCATTCG AGTCCCTTTG TGTTCCATTT
CGCCTTACAG TTTTCTTCAG CTCTTTAGAT CTACAAAAAA 2140

2141 ATG TCG GAC GTA GAG ACG TTT GCT TTC CAG GCT GAG ATC AAT CAG CTT CTC AGT
      M   S   D   V   E   T   F   A   F   Q   A   E   I   N   Q   L   L   S
2195 CTT ATC ATC AAC ACT TTC TAC AGC AAG GAG ATC TTT CTC CGT GAA CTC ATC
      L   I   I   N   T   F   Y   S   K   E   I   F   L   R   E   L   I
2249 AGC AAT TCT TCC GAT
      S   N   S   S   D

GTAAGTCTCC GACGGTTTAG TTTTTTTTAT CTTCTAGGAT ACTGTGGTTT TACTGCTCTT TCATAGTTTA
AAATTTGATT ATTCTAGAGC GATCTGAGCT CTTTTTTATT GTCTTCGGAG AAAGCTTAAC GTGATCTATG
                                  ....
TGATTTTGAA GTTTGATTAT TAGAGAGCAG CATCAATTTT TTTTGAGTTT TTATATGTAT TTTGTTGGTG
```

FIGURE 2B

```
TATAGCTTAA CGTGATCTTC TAGGATACTG TAGGTGCTAT AATTTTGAAG CAATGATTAT TTTAGATCAG
TTTATTTTCT ATGTGGAGGT TATATGCTTA TCTGTATTGT TGTTGTTGAT AGCTTAAGGT GATCTTCCAG
CATACACTGT AGTGCTATGG CGCTCTTTGA TTAAGAACTG TGATTATTTT AGAGCAGCTG AGTATTTTTG
TGAGTTTTTT CATATGTATT CTATATATGG ATAGCTTGAT GTGATTGTCT GGGATACTGC TGTTCCACAG
TGCTCTGTCT GGATCGTTCA GAGCTTCTGT TTTGGCATCT TAATACTTAG GTGATAGGAG TGAGTATTTA
GCCTGCCGTG TATCTCCAAT GGTAATTAAA AATTTGCCTG GTTTGTGTAT CGTGTCTTCT AGATACCTAG
TCTGAACATA TGTATCATCG TAGTGTTAAT TATATGATTT TCACTATGAT ATACCATAGT GCCATCGACC
TCTGTGACTG CGCAAAATAA TTTGAGTAAT TTAGAGCACC TAATTCAATG TTCTGCTTTG TCGTCATAAT
AAGAGTTTAT CTAGTTGTCC TATTCTTGTT CAGACTAGGT AATGCAGATA CAAGTCTGAA TTTGATTGT
CCGATCAGCT AATTAAATCA ATATGTTTCT GGTTGAGGGA TTCGGTTCTG TTATCTGGAT CTATTATATC

ACAGGAAATG AAATGTTTGT TCTTACTTGG TTGTTAATTG TATGCCATAT TTGATATTTT TTTGTATTTT
GGGATTATAC TTTTAG

3260 GCT CTA GAC AAG ATC CGC TTT GAG AGT TTA ACC GAC AAG AGC AAG CTA GAT GGT
     A   L   D   K   I   R   F   E   S   L   T   D   K   S   K   L   D   G

3314 CAA CCA GAG CTC TTC ATC CAT ATT ATT CCA GAC AAG GCC AAT AAT ACT CTC ACT
     Q   P   E   L   F   I   H   I   I   P   D   K   A   N   N   T   L   T

3368 ATC ATT GAT AGT GGT ATT GGT ATG ACA AAG GCT G
     I   I   D   S   G   I   G   M   T   K   A   D

GTAAGTAGTA GGGACATATT GGAAGCTAGA AGCTCAACCA GAGTTTCATC TATATTATCT GTTCTTAATG
TTGCATTTCT ATTTGCTGAC CTTCTTTGTT TTATTGCAG AT

3514 CTG GTG AAT AAC CTG GGT ACA ATT GCA AGG TCA GGA ACC AAG GAG TTC ATG GAA
     L   V   N   N   L   G   T   I   A   R   S   G   T   K   E   F   M   E

3568 GCT CTT GCA GCT GGT GCT GAT GTT AGC ATG ATT GGT CAA TTC GGT GTA GGT TTC
     A   L   A   A   G   A   D   V   S   M   I   G   Q   F   G   V   G   F
```

FIGURE 2C

| | | | | | | | | | | | | | | | | | |
|---|---|---|---|---|---|---|---|---|---|---|---|---|---|---|---|---|---|
| 3622 | TAC Y | TCT S | GCT A | TAC Y | TTG L | GTA V | GCT A | GAG E | AAG K | GTT V | GTG V | ACC T | ACA T | AAG K | CAC H | AAT N | GAT D |
| 3676 | GAT D | GAG E | CAA Q | TAT Y | GTC V | TGG W | GAG E | TCT S | CAA Q | GCC A | GGT G | GGC G | TCT S | TTC F | ACT T | GTT V | ACC T | AGG R |
| 3730 | GAT D | ACA T | TCT S | GGT G | GAG E | AAC N | CTT L | GGT G | ACC T | AGG R | ATG M | TCT S | GTC V | TTT F | CTT L | TAT Y | CTC L | AAG K |
| 3784 | GAG E | GAT D | CAG Q | CTT L | GAA E | TAC Y | CTT L | GAA E | CGT R | AGG R | CTC L | AAG K | GAC D | GTC V | CTG L | ATT I | AAG K | AAG K |
| 3838 | CAC H | TCT S | GAG E | ATT I | AGC S | TAT Y | CCT P | ATT I | TCT S | CTG L | TGG W | GTT V | GAG E | GAG E | AAG K | ACC T | ATA I | GAG E |
| 3892 | AAG K | GAA E | ATT I | TCT S | GAT D | GAT D | GAG E | GAG E | AAG K | GAG E | AAA K | GAG E | AAG K | AAA K | GAT D | GAG E | GGA G | AAG K |
| 3946 | GTA V | GAG E | GTT V | TCC S | AAT N | GAG E | ATC I | GAG E | TCA S | CTG L | GTG V | AAC N | CTG L | GTG V | CCT P | ATT I | AAG K | GTC V |
| 4000 | AAA K | GAA E | CCA P | GAA E | GAG E | AAG K | ACA T | AAG K | GAA E | TAT Y | GCT A | TAC Y | TTC F | TAC Y | AAG K | TGG W | ATG M |
| 4054 | AGA R | AAG K | CCA P | GAA E | GAG E | ATC I | ACA T | CTT L | CAT H | CTT L | TTT F | GCT A | CAC H | TAC Y | TTC F | GCT A | AGC S | TTG L |
| 4108 | ACT T | AAT N | GAT D | TGG W | GAA E | GAG E | GCT A | GTT V | TTT F | AAC N | AAG K | CAG Q | AGG R | TAC Y | CCT P | TAC Y | GGT G | CAG Q |
| 4162 | TTG L | GAG E | TTC F | AAG K | AAG K | GCT A | AAG K | CCC P | GTC V | ATC I | AAG K | CCA P | AAA K | TTG L | TAT Y | GTT V | TTT F | TTT F |
| 4216 | GAC D | ACA T | AAG K | AAC N | TGT C | GAT D | GAG E | TTG L | AAC N | ATT I | CCT P | GAA E | TAT Y | TTG L | AGC S | GCT A | CGT R | GTG V |
| 4270 | ATG M | GAT D | C | D | E | L | I | P | E | Y | L | S | V | F | I | G | I | |

FIGURE 2D

```
4324  GTG GAT TCT GAG GAC CTT CCT CTC AAC ATC TCC AGA GAG ACA TTG CAG CAG AAC
       V   D   S   E   D   L   P   L   N   I   S   R   E   T   L   Q   Q   N

4378  AAG ATC CTA AAG ATT CGC AAG AAT TTG GTG AAG AAG TGT TTC GTT GAG CTT TTC
       K   I   L   K   I   R   K   N   L   V   K   K   C   F   V   E   L   F

4432  TTT GAA ATT GCT GAG AAC GAG ATC TAC AAT GAC GAG TTC TAT GAG GCG AAG TTT TCT
       F   E   I   A   E   N   E   I   Y   N   D   E   F   Y   E   A   K   F   S

4486  AAA AAC CTC AAG CTT GGA ATC CAT GAG TCT CAG AAC AGG ATG GCA AAG TTT GCT
       K   N   L   K   L   G   I   H   E   S   Q   N   R   M   A   K   F   A

4540  GAA CTG CTG AGG TAC CAC ACT TCC AAG GGT GAT GAG ATT TAC ACC TTG AAG
       E   L   L   R   Y   H   T   S   K   G   D   E   I   Y   T   L   K

4594  GAC TAT GTG ACC AGA ATG GTT CAG GGC AAT GAG ATT TAC AAA CTG ATT ACT GGT
       D   Y   V   T   R   M   V   Q   G   N   E   I   Y   K   L   I   T   G

4648  GAG AGC AAG AAG GCT GTT TCT GAT GCC ATT TTC GAG TAT CTG AAG CTC CAG
       E   S   K   K   A   V   S   D   A   I   F   E   Y   L   K   L   Q

4702  GGA TAT GAG GTG CTT TAC GGC AAA GTT GAT GAT GAG GAA TAT AAG GAG AAG
       G   Y   E   V   L   Y   G   K   V   D   D   E   E   Y   K   E   K

4756  CTG AAG GAA TTT GAG AAG AAG AAG CTT GTT AAG CAG GAA ACC AAG TCA CTC AAG TTT
       L   K   E   F   E   K   K   K   L   V   K   Q   E   T   K   S   L   K   F

4810  CTT GAT GAG AGT GAT GAG ATG GTG TCT GCT GAA CAG TTG AAA GAT GAG AAG GTC
       L   D   E   S   D   E   M   V   S   A   E   Q   L   K   D   E   K   V

4864  GAG GGA CTG TGT CTA GGA GAT GTG CCC TGC CTA GGA GAA TTG AAA GTT ACT GGT TAT
       E   G   L   C   L   G   D   V   P   C   L   G   E   L   K   V   T   G   Y

4918  ATT GTT TCT GAC CGT GTT GTT GAC TGT TTG CAG GCA AAG AAG GAG
       I   V   S   D   R   V   V   D   C   L   Q   A   K   K   E

4972  GGC TGG ACT GCT AAC ATG GAG AGA CAG CAG GCA CTT AGG GAC TCC
       G   W   T   A   N   M   E   R   Q   Q   A   L   R   D   S
```

FIGURE 2E

```
5026 AGC ATG GCT GGA TAC ATG TCT AGC AAG AAG ACC ATG GAG ATC AAC CCA GAG AAC
      S   M   A   G   Y   M   S   S   K   K   T   M   E   I   N   P   E   N

5080 TCC ATC ATG GAT ATG TTG AGG CTA GAG AGG GCT GAC GCA GAC AAG AAT GAC AAG TCT
      S   I   M   D   M   L   R   L   E   R   A   D   A   D   K   N   D   K   S

5134 GTG AAG GAC TTG GTT CTT TTT GAG ACT GCC CTT CAC ATT CTC AGG ATG TTG AAA CTC
      V   K   D   L   V   L   F   E   T   A   L   H   I   L   R   M   L   K   L

5188 AGC CTC GAG GAG CCA AAC TTT GGC AAC AGA ATT CAC AGG ATG ATG GAC ATG CCA GCA TTG
      S   L   E   E   P   N   F   G   N   R   I   H   R   M   M   D   M   P   A   L

5242 GGT TTG AGC ATT GAT GAG AGC GGA GAT GCT GAT GAG ATG GAG GAG GTT GAT TAA
      G   L   S   I   D   E   S   G   D   A   D   A   M   E   E   V   D   *

5296 GAG GAT CCT GAA GCT GAT GCT AAG ATG
      E   D   P   E   A   D   A   K   M

GTTCATTAAT GTTTGATAG TTTTATGGGT TCCTTTACTA CTACTTTATT CCCTAGTTTT TGCTTTATCC
CATCAGAACA ATATGTGAGG GTTTAATGC CGTTCTTTTA GAATGGCAGT TCAATGTTAG GTTATAATTC
TCTTTTTGT TTTGACATTC GTGGTTGATA TAGTTTATTT TCTTGCCC
                                                     5534
```

FIGURE 2F

```
MSDVETFAFQAEINQLLSLIINTFYSNKEIFLRELISNSSDALDKIRFESLT
•••a••••• •• ••••••a•••••••••••••••m•••••••• a••a
                                              104
DKSKLDGQPELFIHIIPDKANNTLTIIDSGIGMTKADLVNNLGTIARSGTKE
•  aa•a  ya•y• •a• a    a•a•a•y•••••ya•d•••••••• ••••
                                              156
FMEALAAGADVSMIGQFGVGFYSAYLVAEKVVVTTKHNDDEQYVWESQAGGS
••••• ••••y••••••••••••aa••• a• •ad• ••••••d••• ••••
                                              208
FTVTRDTSGENLGRGTKMVLYLKEDQLEYLEERRLKDLIKKHSEFISYPISL
•••y •m  • d••••a d•d••a••y•••••m••• ay•m••y•a ••• •
                                              252
WVEKTIEKEISDDEEE---EEKKDEE---GKVEEVDEEKEKEEKKKKKVKEV
•a•  •••maaa•y•   y••yyy•   • •y•y•y ••+ a•a••y••
                                              304
SNEWSLVNKQKPIWMRKPEEITKEEYAAFYKSLTNDWEEHLAVKHFSVEGQL
 •   •• •••• • •   •• ••• y•••aa•••• a•a•••••••••••
                                              356
EFKAVLFVPKRAPFDLFDTKKKPNNIKLYVRRVFIMDNCDELIPEYLSFVKG
•• • ••m•y•••••••  ••• •••••••••••••a•damm••••a•y•y••
                                              408
IVDSEDLPLNISRETLQQNKILKVIRKNLVKKCVELFFEIAENKEDYNKFYE
••••••••••a••• ••••••a••••••d•••m •a• •a•• a• a •••m
                                              460
AFSKNLKLGIHEDSQNRAKFAELLRYHSTKSGDEMTSLKDYVTRMKEGQNDI
•••••a•••m•••ay•••  •m••• ••y•a••m••• •••y•a• •  •
                                              512
YYITGESKKAVENSPFLEKLKKKGYEVLYMVDAIDEYSIGQLKEFEGKKLVS
•••••••ayy•ya•y•ya y•mya ••yaa y •••• d •••••y•• ••a
                                              564
ATKEGLKLDESEDEKKKQEELKEKFEGLCKVMKDVLGDKVEKVIVSDRVVDS
••aaa • • a ••aa ayy•y a• •a• a• •yya••••m•• a a•a
                                              616
PCCLVTGEYGWTANMERIMKAQALRDSSMAGYMSSKKTMEINPENSIMDELR
•aa a•y m••m••••••••••••••y•y a₁•yy••y ••a•  • y•a
                                              668
KRADADKNDKSVKDLVLLLFETALLTSGFSLEEPNTFGNRIHRMLKLGLSID
yyadaaaa•• ••••ad••a••••y•••••my• my m•• •a•a••• ••
                                              699
EESGDADADMPALEDPEADAEGSKMEEVD
••    d    d    dy          •••••
```

FIGURE 3

```
                                          Tth111I           Eco57I
                                            —                 —
  1 GGAAGAGAGCTGATGCTGATAAGAATGACAAGTCCGTCAAGGATTTGGTTCTATTGTTGTTTGAGACTG  69
    GlyArgAlaAspAlaAspLysAsnAspLysSerValLysAspLeuValLeuLeuPheGluThrA
                                                   49                  65

Ksp632I                 Tth111I  Ksp632I
           —                       —       —
                                          EcoRI
                                            —  —
 70 CTCTTCTCACTTCAGGTTTCAGCCTTGATGAGCCAAACACATTGGCAACAGAATTC 126
    laLeuLeuThrSerGlyPheSerLeuAspGluProAsnThrPheGlyAsnArgIle
       77                                        122
                                                    124
                                              120
```

FIGURE 4

PLANT PROTEINS, PROMOTERS, CODING SEQUENCES AND USE

TECHNICAL FIELD

The field of this invention relates to compositions and methods for modification of plant phenotype by preferential transcription of a nucleic acid sequence of interest.

BACKGROUND

Various "promoter" sequences are available which may be used in the genetic engineering of plants. Depending upon the transcription initiation characteristics desired (strength, tissue specificity, developmental specificity, etc.), different promoters are available which may be employed to initiate the transcription, and in some cases the translation, of a DNA sequence of interest joined at the 3' end of the promoter region.

For example, promoters, or "transcription and translation initiation regions," known as 35S Cauliflower Mosaic Virus (CaMV 35S), mannopine synthase (mas) and octopine synthase (ocs) have been used successfully to direct the expression of desired nucleic acid sequences in transformed plant tissue. The relative activities of these promoters may be ranked: CaMV 35S >mas >ocs. When expressed in a transgenic plant, DNA sequences under the control of these promoters are found at relatively low levels and expressed fairly evenly (i.e., constitutively) throughout the plant. A variation of the CaMV 35S promoter, known as the "double 35S promoter (D35S)" because of repeated CaMV 35S sequence engineered into the promoter, shows markedly stronger transcription initiation properties than the "unenhanced" CaMV 35S.

Transcription and translation initiation regions also have been developed from indigenous plant genes, especially when differentially specific characteristics are desired. One example of such a promoter is the "2AII promoter" described in WO 88/09334; a nucleic acid sequence under the regulatory control of the 5' noncoding region of the tomato 2AII gene will be preferentially transcribed in developing fruit tissue.

Of particular interest is the discovery of promoters which demonstrate enhanced transcription initiation characteristics in rapidly dividing cells or rapidly growing tissue, against stress or other detrimental factors. For example, the site of action of various herbicides is rapidly dividing cells. Insects frequently target young tender tissue for attack resulting in injury at this site. Certain plant diseases are particularly severe with young rapidly dividing cells. Also, the tender new tissue is most sensitive to stresses such as frost, so that enhanced production of products which protect against frost or inhibition of endogenous products which enhance the sensitivity to frost is of primary interest in such tissue.

Likewise, there are advantages with the increased expression of a DNA sequence of interest under the regulation of an inducible promoter. Such promoters may regulate the expression of genes in response to a variety of different environmental factors, such as light, wounding, exposure to heavy metals, and/or temperature, for example.

Heat stress in particular can be a problem in many useful agronomic crops. In the laboratory, heat shock is a useful tool to study the effect of a given DNA sequence under controlled conditions. Regulating a gene's activity by heat shock might also be used to control plant features for a given period of time to alter and/or control a biochemical pathway, express controlled amounts of otherwise toxic substances, or the like, in the heat shock affected tissues. Thus, the enhanced production of desired DNA sequences under the control of a heat shock induced promoter could allow for the genetic engineering of plants with improved heat tolerance for field use. Alternatively, heat induced promoter activity might be a useful "switch" for the induction of a desired characteristic for a given period of time under otherwise controlled conditions.

Plant stress may also be induced by wounding. As noted above, insects often selectively chew on young tissue. Wound stress can also occur in older, more mature tissue, as a result of breaking, cutting, chewing, boring, and the like. Some promoters are believed to display wound-inducible characteristics, although they are often selective to "crush" or "chew" type wounds and do not offer a wound response to "cutting" or "excision" type wounds. Broad spectrum wound promoters are desired.

Thus, the discovery of new promoters with useful transcript initiation patterns, especially ones having very strong promoter activity, are desired for the controlled expression of desired nucleic acid sequences. Promoters which show enhanced activity in rapidly dividing tissue and/or show enhanced activity induced by environmental phenomena are of special interest for many genetic engineering applications in plant tissue. Protein sequences associated with such promoters may also provide useful genetic engineering tools to enhance plant characteristics generally, as these critical gene sequences are abundant in young or stressed plant tissue.

In addition, sequence enhancers which could confer high expression to plant or animal DNA sequences associated therewith are desired to improve expression levels of flanking sequences, generally. In some non-plant species, particular sequences found flanking certain genes have been postulated to bind to the "nuclear scaffold."

The nuclear scaffold is comprised of non-histone proteins, such as topoisomerase II (Earnshaw, et al., J. Cell Biol. (1985) 100:1706–1715). Chromatin loops are attached to the scaffold at specific DNA sequences (Gasser & Laemmli, Cell (1986) 46:521–530) located at the base of the loops. Attachment sites are found in both 5' and 3' untranslated regions.

RELEVANT LITERATURE

European Patent Application 330 479 describes the isolation of a gene, corresponding to a 26kDa hsp protein, from soybean, and presents methods for using the regulatory regions of the gene to achieve stress-induced expression of a plant-expressible structural gene. A study of the expression of heat shock induced mRNAs in soybean in response to other environmental stress factors is reported by Czarnecka, et al., Plant Molecular Biology (1984) 3:45–58. The induction, in maize mesocotyls, of mRNA corresponding to a heat shock protein (hsp70) by heat shock, water stress, abscisic acid and wounding is reported by Heikkila, et al., Plant Phys. (1984) 76:270–274.

Transcript initiation regions of proteins in the size range of about 80 to 90 kd, induced through heat shock, have been obtained from various prokaryotic and animal sources. (See generally, Linquist, S. Ann.Rev.Biochem. (1986) 55:1151-1191.) This "class" of heat shock proteins is often referred to as "hsp83," after the well-studied Drosophila protein. Yeast heat shock proteins are called hsp90. Hackett & Lis, Nucl. Acids Res. (1983) 11:7011-7030 (Drosophila melanogaster); Farrelly & Finkelstein, J.Biol.Chem. (1984) 259:5745-5751 (Saccharomyces cerevisiae). Related, highly homologous, proteins of 100 to 110 kd are found in mammalian cells. Kulomaa, et. al., Biochemistry (1986) 25:6244-6251.

BRIEF DESCRIPTION OF THE DRAWINGS

FIG. 2 shows approximately 2.1 kb of 5' non-coding region, all of the coding region, and the 3' transcribed, non-coding sequence of the hsp80 genomic clone, Ghsp-4 (locus A) including all of pCGN7117 and partial sequence of pCGN7126.

| Key to symbols: | |
|---|---|
| . . . | homology to scaffold attached regions |
| A box: | AATAAATAAA or T Box: TTATTTTTTT |
| +++ | homology to heat shock element |
| ••• | TATA box |
| §§§ | transcriptional start as determined from primer extension assays |

FIG. 3 shows conserved amino acids in the plant hsp80 protein. Symbols mark residues conserved in: ·, animals; y, yeast; d, Drosophila; m, at least some mammals; —, residues missing from plant hsp80.sequence comparisons between tomato and other heat shock proteins (yeast, Ia, and chicken).

FIG. 4 shows approximately 126 bp of analogous sequence of the hsp80 genomic clone, Ghsp-7 (locus B), which corresponds to nucleotides 1618-1742 of clone 7115.

Figure 5:
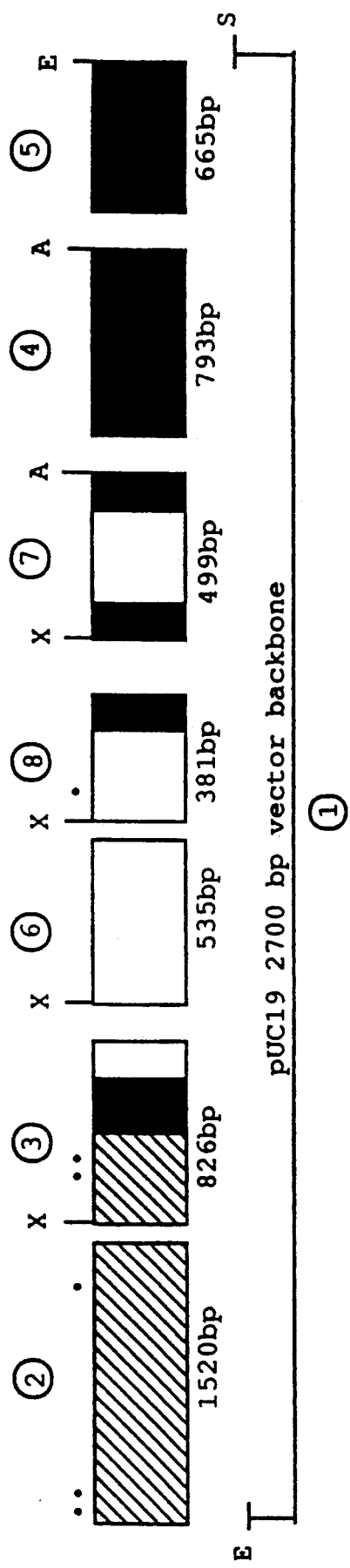

FIG. 5 shows a representation of pCGN7117 digested with XbaI ("X"), Asp 718 ("A"), EcoRI ("E"), and SalI ("S"). The hatched shading indicates promoter region, the black shading represents coding region, and the white boxes represent introns. The "." symbols are representative of scaffold attachment regions (SAR) found in those sequences. The number assigned to each fragment is a ranking by size.

SUMMARY OF THE INVENTION

In a first embodiment, this invention relates to an isolated tomato heat shock protein (hsp80) or a nucleic sequence obtainable therefrom. The sequence may be RNA, cDNA, fragments of the genomic sequence, and the like.

In a second embodiment, this invention relates to DNA sequences comprising the 5' non-coding region obtainable from a tomato hsp80 gene comprising the transcription initiation region and free of the intact plant hsp80 coding region. In a more preferred embodiment, the 5' non-coding region includes both the transcriptional and translational initiation regions from the same gene source. These transcriptional and translational initiation regions may be placed upstream of a DNA sequence of interest which is different from the hsp80 coding region. This DNA sequence of interest may encode a structural gene or may comprise nucleotides in an anti-sense orientation. The transcriptional and translational termination regions may be provided as a feature of the DNA sequence of interest or may be engineered specially into the DNA sequence. In a preferred embodiment, the 3' non-coding transcriptional and translational termination region is closely homologous with the native 3' non-coding region of the 5' transcription initiation non-coding region.

In a further embodiment, this invention relates to transgenic plant cells containing an expression cassette, which are capable of expressing a DNA sequence of interest under the transcriptional and translational initiation regulatory control of a promoter obtainable from the tomato hsp80 gene. The DNA sequence of interest is other than an intact sequence of said hsp80 gene. The transcription and translation termination regions of the expression cassette may be provided as a feature of the DNA sequence of interest or may be engineered specially into the expression cassette. In a preferred embodiment, the 3' non-coding transcriptional and translational termination region is obtained from the same gene as said 5' non-coding region.

This invention also relates to whole plants, transformants and progeny, which will express an inserted foreign DNA sequence under the regulatory control of a promoter obtainable from tomato hsp80.

DETAILED DESCRIPTION OF THE INVENTION

Novel nucleic acid sequences, constructs employing such sequences, transgenic plant cells and plants are provided employing sequences associated with tomato heat shock protein 80.5 ("hsp80"). Nucleic acid sequences obtainable from the use of hsp80 as a probe in other plant species are also disclosed. In particular, the 5' non-coding region of tomato hsp80 or other plant promoters obtainable therefrom, especially to provide differentially specific initiation of transcription of a desired nucleic acid sequence of interest. Also provided are putative sequences believed to represent Scaffold Attachment Regions (SAR) of the plant hsp80 gene.

Tomato hsp80 is characterized by having a mRNA of about 2.3 kb, two introns, a predicted pI of about 4.69, and a molecular weight of 80,479.8 daltons. In the direction of transcription, the first intron is approximately 995 bp in length and the second is approximately 109 bp in length. The polypeptides encoded by tomato hsp80 have substantial homology with the polypeptides encoded by related heat shock proteins from a wide variety of prokaryotic and eukaryotic species. The native protein encoded by tomato hsp80 has a molecular weight of approximately 80.5 kd.

Evidence indicates that there are two hsp80 genes in tomato, identified herein as locus A and locus B. The low copy number of the hsp80 gene is a useful indicator of the actual "strength" of the promoter. In gene families where several gene copies exist, high expression levels may be the result of the combined gene activities. Thus, the low copy number indicates that the hsp80 promoter may find application where high level expression of a given DNA sequence of interest is desired in meristem tissue and/or in response to a stress event.

Among multi-gene families it is desirable to find the transcriptional initiation regulatory region which provides a high level of transcription. Thus, the transcriptional initiation regulatory region should provide for at least about 10% of the total hsp80 mRNA, preferably at least about 20%, and more preferably at least about 30%. This can be determined by employing two probes, one probe which is conserved and binds to all hsp80 mRNA, and the other probe being in a polymorphic region of the hsp80 locus which binds uniquely to the hsp80 gene being assayed. Preliminary data suggest that the B locus may contribute about 50% of the hsp80 mRNA. In the present invention, hsp80A and hsp80B are 95% homologous at the nucleotide level and are distinguishable by differences in 3' non-coding sequence.

Tomato hsp80A message is found in abundance in most, if not all meristematic tissues, e.g. flower meristems, early fruit, and root and shoot apices, representing about 1% of the total mRNA in these tissues. hsp80A message is detected in floral primordia of immature fruit, where it increases until the fruit begins to swell, approximately 5 to 8 days after anthesis. The RNA message in normal mature leaves is found at approximately 1/10th of the level observed in meristematic tissue. The RNA message is found at enhanced levels, approximately a 2-3 fold increase in mature leaf tissue subsequent to heat shock. No appreciable effect is observed on the level of hsp80A found in root tips or shoot tips as a result of heat shock.

The region found immediately 5' upstream to the hsp80 coding region provides for the initiation of transcription and translation of the hsp80 structural gene. For some uses the transcription initiation region may be used without translation initiation sequences, such as when the hsp80 transcription initiation region is used to regulate the transcription of a DNA sequence of interest in an anti-sense orientation. The transcription initiation region includes transcriptional control regions such as "TATAA"and "CAAT" box sequences as well as sequences which will regulate the timing and tissue specificity of the transcribed product. The hsp80 translation initiation region, ribosome binding site and other related sequences associated with protein expression of mRNA sequence of the "ATG" start codon, are preferentially used in conjunction with the hsp80 transcription initiation region. The "ATG" start codon is often provided by the DNA sequence of interest. The use of the hsp80 transcription/translation initiation regions in combination is termed the "hsp80 promoter." Alternatively, in some embodiments, the transcription or translation initiation regions of the hsp80 may be combined with other 5' non-coding regions to create heterologous promoters.

The hsp80A transcript initiation region of this invention shows strong expression in the apical 5 mm region of the root, those cells undergoing cell division and elongation. Expression is very low in mature roots except in the cambial region. Apical shoots have a high level of expression in the apical, residual and ground meristems. In flower meristems, regions of higher activity within the meristem appear to be regions of sympodial growth. As noted above, hsp80A mRNA is not significantly affected by heat shock in the meristematic tissues. In other words, the hsp80A promoter provides consistently high levels of expression in these meristematic tissues and may be used to regulate the expression of a DNA sequence of interest in such tissues in a like fashion.

Relatively low levels of hsp80 protein have been found in mature tissue. When stress is induced, however, the message level in mature leaves is observed to increase 2-3 fold. Thus, the hsp80 transcript initiation region of this invention provides enhanced transcription in some plant tissues, such as mature leaf tissue, as a result of heat shock, wounding or other such stress, and may be used to regulate the expression of a DNA sequence of interest nn such tissues in a like fashion.

By this invention, tomato hsp80 sequences are provided: amino acid sequence/cDNA sequence of the hsp80 protein (FIG. 1) and approximately 2.3 kb of the 5' non-coding region of the tomato hsp80 gene (FIG. 2). These sequences may be used to identify plant hsp80 genes from plant sources other than tomato.

Plant hsp80

The plant hsp80 sequence may be isolated from any convenient plant. When used in a construct, the hsp80 sequence may be endogenous to the target host or exogenous to the target host. Plants from which hsp80 may be isolated include fruit, vegetables, oil seeds, fiber sources, grasses, trees, flowers, grain, ornamentals and the like. Particular plants of interest include tomato, pea, tobacco, maize, soybean, Brasslca, cotton, wheat, alfalfa, turf grass, and the like.

Particularly, by identifying sequences of the subject plant associated with the hsp80 gene, which sequences are conserved in species other than plants, these conserved sequences may be used as probes for hybridization to cDNA obtained from a number of different plant sources. Examples of the sequence homology between tomato hsp80 and other heat shock proteins is found in FIG. 3. Tomato hsp80 protein is about 65% homologous to yeast hsp90.

Usually, the probe sequence will have at least about 60%, preferably at least about 70%, identity of base pairs, excluding any deletions which may be present. cDNA libraries prepared from the plant source of interest may be probed with the conserved hsp sequence probe and used to identify other respective plant cDNA sequences corresponding to hsp80. Conveniently, the target cDNA may be cloned in a virus, so that hybridizing phage may be plaque-purified. The identified cDNA may be further subcloned and the sub-clone sequence analyzed and used for production of probes. The probes are then used to identify cDNA hsp80 sequences in a cDNA library of the plant source of interest. The cDNA is used to identify geonomic sequences in a plant genomic library of the appropriate plant species and the positive clones analyzed by restriction enzyme digestion, DNA sequencing or the like. The level of transcription may then be determined in a variety of plant tissues to demonstrate the pattern of transcription in the plant. In this manner, one or more sequences may be identified providing both the coding region, as well as the transcriptional regulatory elements of the gene.

Probes can be considerably shorter than the entire sequence, but should be at least about 10, preferably at least about 15, more preferably at least about 20 nucleotides in length. Longer oligonucleotides are also useful, up to the full length of the gene encoding the polypeptide of interest. Both DNA and RNA probes can be used.

In use, the probes are typically labeled in a detectable manner (for example with $^{32}$P-labeled or biotinylated nucleotides) and are incubated with single-stranded DNA or RNA, which is typically immobilized on a nitrocellulose or nylon filter, from the organism in which a gene is being sought. In this way, nucleic acids which hybridize to the probe may be identified. Hybridization techniques suitable for use with oligonucleotides are well known to those skilled in the art.

Although probes are normally used with a detectable label that allows for easy identification, unlabeled oligonucleotides are also useful, both as precursors of labeled probes and for use in methods that provide for direct detection of DNA or DNA/RNA. Accordingly, the term "oligonucleotide" refers to both labeled and unlabeled forms.

Once the 5'- and 3'-non-coding regions of the hsp80 gene have been identified, they may be manipulated in accordance with conventional methods. Where a convenient restriction site is present downstream from the ATG initiation codon, it may be useful to cut at that site and insert a DNA sequence of interest for transcription under the regulatory control of the hsp80 regulatory elements. Where a convenient restriction site is present immediately upstream from the ATG initiation codon, a functional translation region may be engineered. An ATG codon and appropriate leader sequence may be provided by the DNA sequence of interest or engineered as separate components, from a promoter for example. Where the DNA sequence of interest is a structural gene, the sequence of interest will be inserted so as to be in reading frame with the upstream codons and the initiation methionine. Where the DNA is to be used as an anti-sense sequence, it need not be in reading frame with the upstream codons.

In order to prepare convenient restriction sites for insertion of a DNA sequence of interest between hsp80 5' and 3' regulatory regions, oligonucleotides which are complimentary to the 5' and 3' ends of the sequence of interest are synthesized on an Applied biosystems model 380A DNA Synthesizer (Applied Biosystems; Foster City, CA). The first oligonucleotide is complimentary to the 5' end of the sequence of interest, and, in addition, has a restriction site at the 5' end. The second oligonucleotide comprises sequence that is complimentary to the 3' end of the sequence of interest, and, in addition, has a restriction site at the 5' end. When a PCR reaction is carried out according to the manufacturer's instructions (Perkin-Elmer Cetus; Emeryville, CA) using the above oligonucleotides as primers and DNA containing the sequence of interest as template, the PCR product is a fragment containing restriction sites at either end of the DNA sequence of interest. This fragment may be digested with restriction enzymes which recognize the added restriction sites and ligated with hsp80 regulatory regions.

Usually, not more than 20 codons at the 5'-end of the hsp80 coding region will be retained. Preferably, the sequence of interest will not be fused to the 5'-region of the hsp80 coding region but rather may be joined to the transcriptional initiation regulatory region of hsp80 in a variety of ways. By blunt-end ligation of the gene of interest to the various hsp80 fragments, one can screen for expression of the gene of interest, indicating that a functional transcription initiation region has been retained.

Conveniently, one may identify a convenient restriction site in the 5'-untranslated region of hsp80 and in the 5' region of the gene of interest and employ an adapter which will join the two sequences and restore any lost sequences from the 5'-untranslated region and the 5' region of the gene of interest. Alternatively, one may introduce a polylinker immediately downstream from the 5'-untranslated region, for insertion of the DNA sequence of interest.

The 5'-non-coding region which will be employed for joining to the sequence of interest will usually be at least about 100 bp, and not more than about 10 kbp, frequently being less than about 2 kbp, and may include all or a portion of an intron (including the splice sites). The 5'-non-coding region which is employed will be proximal to (usually within 20 bp) or abut the initiation codon. Therefore, by employing sequence analysis, one can identify the initiation codon of the hsp80 coding region and isolate the upstream region in accordance with conventional ways. Where a particular cloned fragment in a genomic library does not have the desired size, the library may be further screened by walking the 5'-non-coding region until a fragment of the desired length is obtained. The 5'-non-coding region may then be cloned and sequenced and may then be used for further manipulation. As already indicated, in some instances, at least a fragment of the 5'-coding region may be retained.

In a preferred embodiment, a fragment of the 5' non-coding region of the hsp80A gene is used, a fragment from about nucleotide ten before the start codon, position +60 from the start of transcription, to nucleotide −2070. This region has been observed to confer high levels of apical-shoot-tip-specific expression to heterologous genes, as well as other types of regulation found in hsp80.

Plant hsp80 Constructs

The hSp80 transcriptional initiation region may be inserted into a vector for preparing a construct for transcription, and optionally, translation. The 3' terminus of the hsp80 promoter may be joined to a nucleic acid sequence of interest, which may be a structural gene or coding or non-coding sequence where antisense transcripts may be desired. A wide variety of sequences are of interest for transcription, and optionally translation, under the regulation of the hsp80 promoter. For example, various sequences may be employed relating to enhanced resistance to pesticides (such as providing for the expression of a protein toxin derived from Bacillus thurlngiensis) or herbicides (such as provided a gene encoding for a mutated 5-enolpyruvyl-2-phosphoshikimate synthase to provide decreased sensitivity to glyphosate or a gene to provide for the detoxification of bromoxynil), stress (such as provided by gene for superoxide dismutase), temperature changes, osmotic pressure, salinity (such as a gene associated with the overproduction of proline), and the like. Growth may be modulated, either increased or decreased, depending upon the particular need. Anti-sense sequences may be used to reduce growth, for example, alteration of the auxin/cytokinin ratio may be used to alter growth rate and/or morphology. By enhancing or diminishing the expression of an enzyme in the metabolic pathway for the hormone, the ratio may be modulated. Useful phenotypic properties may also be achieved by the expression of anti-sense hsp80 to modulate expression of hsp80 protein.

Depending upon the sequence of interest, the purpose of the transformation and the particular host, other sequences may be included which provide for specific functions. In some instances, it may be desirable to provide for translocation of the expression product from the cytoplasm to an organelle or for secretion from the cell. In this instance, various transit peptides may be employed for translocating the gene of interest to an organelle, such as the chloroplast or mitochondrion, or to secrete the protein into the extracellular space or to the cell surface. Various transit peptides have been employed, such as the transit peptide of the small subunit of the RUBISCO gene, plant EPSP synthase, acyl carrier protein, and the like.

In addition to the promoter and the structural gene, there will be a transcription/translation termination region, which may be the hsp80 termination region or any other convenient termination region. A wide variety of termination regions have been employed, such as termination regions from opine genes, various plant genes, and the like. The particular termination region will usually not be critical to this invention and any convenient region may be employed. In a preferred embodiment, the respective hsp80 termination region is employed in a construct having a plant hsp80 promoter.

In order to obtain enhanced expression, it may be desirable to provide an expression cassette having a 5' non-coding region capable of initiating transcription and one or more of either introns or a 3' non-coding termination region, which are obtainable from tomato hsp80.

The promoter, structural gene and transcriptional and translational termination region provide an expression construct which may be joined to a vector for cloning. At each stage of the preparation of the construct, the resulting product may be cloned and analyzed to insure that the desired product has been obtained. Cloning vectors conveniently will have one or more markers, which will allow for detection of transformants which contain the construct and marker. For the most part markers will provide for toxin resistance or impart prototrophy to an auxotrophic host. Toxin resistance for the most part will be antibiotic resistance, such as resistance to kanamycin and its analogs, e.g. G418, resistance to chloramphenicol, and the like. For the most part cloning will be performed in *E. coli*, so that a replication system functional in *E. coli* will be employed.

Plant hsp80 Scaffold Attachment Regions

Heretofore scaffold binding sites have been described in plants. By this invention, the use of scaffold attachment regions to enhance expression of a plant expression cassette of interest is described.

Scaffold binding sites, known as the $$
\text{T Box (Drosophila)} = \text{TT}\overset{A\phantom{T}T}{\text{TTATTATT}}
$$
and
$$
\text{A Box (Drosophila)} = \text{AATAAACAAA}
$$

are rich is adenine (A) or thymine (T) (Gasser & Laemmli, Cell (1986) 46521:530). Regions substantially homologous to these sequences were observed in the hsp80 sequences. Inserting one or more such sequences into a promoter capable of directing expression in a plant cell, a coding region (either a DNA sequence in the sense or anti-sense orientation) and/or into the 3' non-coding transcription termination region may increase the efficiency of the promoter. The insertion of at least one scaffold attachment region into the 5' non-coding region to achieve enhancement is desirable. More preferred is the use of multiple scaffold binding sites, especially the use of A box and T box regions. Also preferred is the insertion of one or more scaffold attachment regions into the coding region of the DNA sequence of interest in intron or exon sequences. In another preferred embodiment, one or more scaffold attachment regions are positioned flanking an expression cassette of interest. In this manner, the efficiency expression from an expression cassette integrated into the genome of a plant cell will be improved.

The promoter region of any expression cassette may be enhanced. Promoters such as the CaMV 35S, mas, ocs, MAC (see, U.S. Ser. No. 07/477,055, now U.S. Pat. No. 5,106,739), differentially tissue specific promoters such as fruit-specific or seed-specific promoters, other plant hsp80 promoters, and the like, are such choices.

Plant Transformation

Once the expression construct has been prepared and analyzed to insure it has the proper sequence, it may be then be used for introduction into a plant cell. Various techniques exist for introduction of DNA into plant cells. These techniques include A. tumefaciens mediated introduction, electroporation, protoplast fusion, injection, high velocity projectile introduction, and the like. The targets for introduction of the DNA may be tissue, particularly leaf tissue with *A. tumefaciens*, disseminated cells, protoplasts, seeds, embryo, meristematic regions, cotyledons, hypocotyls, and the like.

With *A. tumefaclens* introduction, the construct will be further modified by having one or both T-DNA borders present, bordering the expression construct, particularly the right border. The construct may be introduced into *A. tumefaclens* carrying the vir genes, where the T-DNA-bordered expression construct will be introduced into plant cells infected with *A. tumefaciens*. The plants which may be genetically modified include those plants described as the source of the hsp80gene. Thus, of particular interest are those crops associated with food sources, such as grain, vegetables and fruits, oil seed, sugar sources, forage, and legumes.

Once the cells are transformed, transgenic cells may be selected by means of a marker associated with the expression onstruct. The expression construct will usually be joined with a marker which will allow for selection of transformed plant cells, as against those cells which are not transformed. The marker will usually provide resistance to an antibiotic, which antibiotic is toxic to plant cells at a moderate concentration.

After transformation, the plants cells may be grown in an appropriate medium. In the case of protoplasts the cell wall will be allowed to reform under appropriate osmotic conditions. In the case of seeds or embryos, an appropriate germination or callus initiation medium would be employed. For explants, an appropriate regeneration medium would be used.

The callus which results from cells may be introduced into a nutrient medium which provides for the formation of shoots and roots and the resulting plantlets planted and allowed to grow to seed. During the growth, tissue may be harvested and screened for the presence of expression of the expression construct. After growth, the seed may be collected and replanted, or prior to seed formation, the modified plant may be used for fertilizing a different strain or vice versa, so as to provide for a hybrid plant. One or more generations may then be grown to establish that the gene is inherited in Mendelian fashion.

Anti-Sense hso80

Of particular interest is a gene associated with tomato, which has the amino acid and DNA sequence found in the Experimental section. The gene and its accompanying untranslated regions may be used in the anti-sense orientation to inhibit expression in plant cells, so as to reduce growth. By targeting expression of the hsp80 anti-sense RNA to a specific tissue type, the development and growth of that tissue type may be inhibited. Thus, fragments of the gene and the untranslated regions of at least about 12 bp, usually at least about 20 bp may be employed to produce an mRNA which results in reduction in expression of the hsp80 gene.

The invention now being generally described, it will be more readily understood by reference to the following examples which are included for purposes of illustration only and are not intended to limit the invention unless so stated.

EXPERIMENTAL

EXAMPLE 1

Isolation of HSP80 cDNA Clone a. Construction of tomato shoot tip cDNA library

Tomato plants (*Lycopersicum esculentum* var. UC82B) are grown at 25° C., 8 hour night, 500 μE/m²s. Shoot tips averaging 5 mm in size and mature leaves are collected from 3-4- week-old plants and immediately frozen in liquid nitrogen. Roots are excised either from one-week-old seedlings which are surface sterilized and germinated on moistened autoclaved germinating paper (Anchor Paper Co.; St. Paul, MN) or from flats of tomatoes grown in vermiculite. A screen is employed just under the surface of the vermiculite to separate the roots more efficiently from the rest of the plant. The roots are washed clean from the vermiculite and harvested.

Total RNA is extracted using the guandinium thiocyanate method of Colbert et al. (PNAS USA (1983) 80:2248-2252), as modified by Facciotti et al. (Biotechnology (1985) 3:241-246). Poly(A)+RNA is selected from total RNA using oligo-dT cellulose chromatography as described by Maniatis et al., (Molecular Cloning: A Laboratory Manual (1982) Cold Spring Harbor, N.Y).

The poly (A)+RNA isolated from shoot tips is used to construct a cDNA library using the vector primer method described by Alexander (Methods ±n Enzymology (1987) 154:41-64). Briefly, poly(A)+RNA is annealed, in excess, to vector DNA that has been T-tailed at the SacI site using the enzyme terminal deoxynucleotidyl transferase and free dTTP nucleotides. The vector DNA is then used as a primer for the synthesis of the first strand of cDNA by the enzyme reverse MMLV transcriptase (BRL; Gaithersburg, Md.), which transcribes complementary DNA from the RNA template. Terminal deoxynucleotidyl transferase and free dGTP nucleotides are then used to add a string of dGTP residues to both 3' ends of the vector/cDNA complex. At this point there are two cDNA molecules per vector. The vector/cDNA is then digested with restriction endonuclease BamHI. This digestion yields two types of DNA fragments. The DNA that will be cloned into *E. coli* consists of the vector attached to one RNA/cDNA molecule. The other fragment consists solely of RNA/cDNA and cannot be cloned into *E. coli* as it lacks the genetic information necessary for replication. Following the BamHI digestion, a linker DNA of the following sequence

```
                              BamHI  NotI  EcoRI  SacI
5'GATCCGCGGCCGCGAATTCGAGCTCCCCCCCCCC3'
3'    GCGCCGGCGCTTAAGCTCGA5'
``` is added to the reaction. The poly(C) residues of this linker anneal to the poly(G) tail of the RNA/cDNA complexes. Reaction conditions are then altered to allow cyclization of the DNA which now contains BamHI restriction sites at both ends. *E. coli* DNA ligase is added to the reaction to join these ends enzymatically. Finally, the enzymes T4 DNA ligase, RNaseH, and DNA polymerase I (Boehringer-Mannheim, Indianapolis, IN) are added to the reaction so that the original RNA template is removed and replaced with DNA. The cDNA (containing plasmid), which now consists of double-stranded cDNA plus vector, is then transformed into competent *E. coli* DH5 a cells (BRL; Gaithersbrrg, Maryland), amplified by plating and scraping colonies, and stored as frozen *E. coli* cells in 10% DMSO at −80° C.

b. Screening of the shoot tio cDNA library

Isolated colonies from the library are transferred to flat-bottomed microtiter dishes containing 150 ml colony storage medium ([10 g Bactotryptone, 5 g yeast extract, 5 g NaCl =Luria Bertani Broth (LB)], 6.3 g $K_2HPO_4$, 1.8 g $KH_2PO_4$, 0.45 g Na-Citrate, 0.09 g $MgSO_4 \cdot 7H_2O$, 0.9g $(NH_4)_2SO_4$, 44 g (35 ml) glycerol in a 1 liter volume) with 50 μg/ml ampicillin. These colonies are incubated overnight at 37° C. on damp paper towels in a sealed plastic bag. 2016 colonies (in 21 microtiter dishes) are stamped onto LB plates (2%) agar supplemented with penicillin at 300 μg/ml Each 20×20cm plate is stamped with a replica of these microtiter dishes. Colony lifts are then made as described by Taub and Thompson (Anal. Biochem. (1982) 126:222-230). To identify clones that hybridize strongly to root and shoot tip cDNA probes, and little or not at all to a mature leaf cDNA probe, the filters from the colony lifts are probed with first strand cDNA from shoot tips, roots, and mature leaves as described by Gubler and Hoffman, (Gene (1983) 25:263-269). The filters are prehybridized and hybridized in hybridization solution (50% formamide, 5X SSC 5X Denhardt's solution, 50 μg/ml heparin, 100 μg/ml denatured salmon sperm DNA, 50 mM $Na_4PO_4$, pH6.8, 150μg/ml yeast tRNA, and 100 μg/ml poly (A)+RNA) at 42° C. Filters are washed in 0.2X SSC at 65° C., wrapped in plastic wrap, and exposed to X-ray film at −70° C. with an intensifying screen.

Seven clones were characterized in detail. This characterization included Southern analysis (see Example 3 for procedure) to select clones from small gene families, Northern analysis (see part c of this example for procedure) to select clones with the desired expression pattern, in situ hybridization (see Example 4 for procedure) to select for expression in shoot tip and root tip, and DNA sequence analysis (see section d of this example for procedure) to determine homology of cDNA sequences to DNA sequences of other genes.

DNA from each clone highly expressed in the shoot tip and/or root is transferred by Southern blot onto a Zetaprobe nylon membrane (Biorad; Richmond, CA). Clones are nick translated using the BRL nick translation kit (BRL; Gaithersburg, MD) according to the manufacturer's instructions, boiled 10 minutes, separated from unincorporated nucleotides on a Sephadex G-50 (Sigma) spin column, and used as probes to identify any related clones. The hybridization solution contains 50% formamide, 5X SSC, 5X Denhardt's solution, 5mM EDTA, pH8.0, 0.1% SDS, 100μg/ml denatured salmon sperm DNA, and 50μg/ml heparin at 42° C. The blots are washed stringently at 68° C. in 0.2X SSC, 0.1% SDS. Old probes are stripped off the filter in 0.1X SSC, 0.1% SDS at 95° C. for 15 minutes. CsCl purified DNA is isolated for each clone. One μg from 1-4 representatives of each group of clones is slot-blotted according to the New England Nuclear (NEN) GeneScreen Plus manual's instructions. Once again, these blots are probed with cDNA from shoot tip, mature leaf, and root mRNA. The modified Guler and Hoffman protocol is used (5μM cold dCTP). The 42° C.) and wash is used. One clone, 7100, which showed the desired characteristics, was selected for further analysis.

C. Northern analysis

Total RNA is isolated as described above. Northern analysis is carried out according to the protocol described by Fourney, et al. (Focus (1988) 10:5-7), using RNA isolated from shoot tip, root, and mature leaf. The probe used was isolated from cDNA clone 7100 by excising the cDNA insert from the plasmid vector and purifying the cDNA fragment by gel electrophoresis. The fragment is labeled with 32P[dCTP]by nick translation (nick translation kit, Gibco-BRL; Grand Island NY). Hybridizations are carried out in a solution containing 50% formamide, 1M NaCl, 1% SDS and 100 μg/ml sheared salmon sperm DNA. Blots are washed in 0.2X SSC, 1% SDS, and exposed to X-ray film. Results show a transcript of approximately 2.3 kb in length.

d. DNA sequencing of cDNA clone 7100

The cDNA insert of clone pCGN7100 was sequenced using the dideoxy chain termination reaction of Sanger, et al. (PNAS USA (1977) 74:5463-5467) employing the Sequenase sequencing kit (U.S. Biochemical Corporation; Cleveland, Ohio). The DNA sequence shows strong homology to the yeast hsp90 and fruit fly hsp83 gene and is thus identified as a plant hsp80 sequence. The 5' terminal portion is used to rescreen the cDNA library to identify a longer (full length) clone.

e. Rescreening of the cDNA library

Figure 1H:
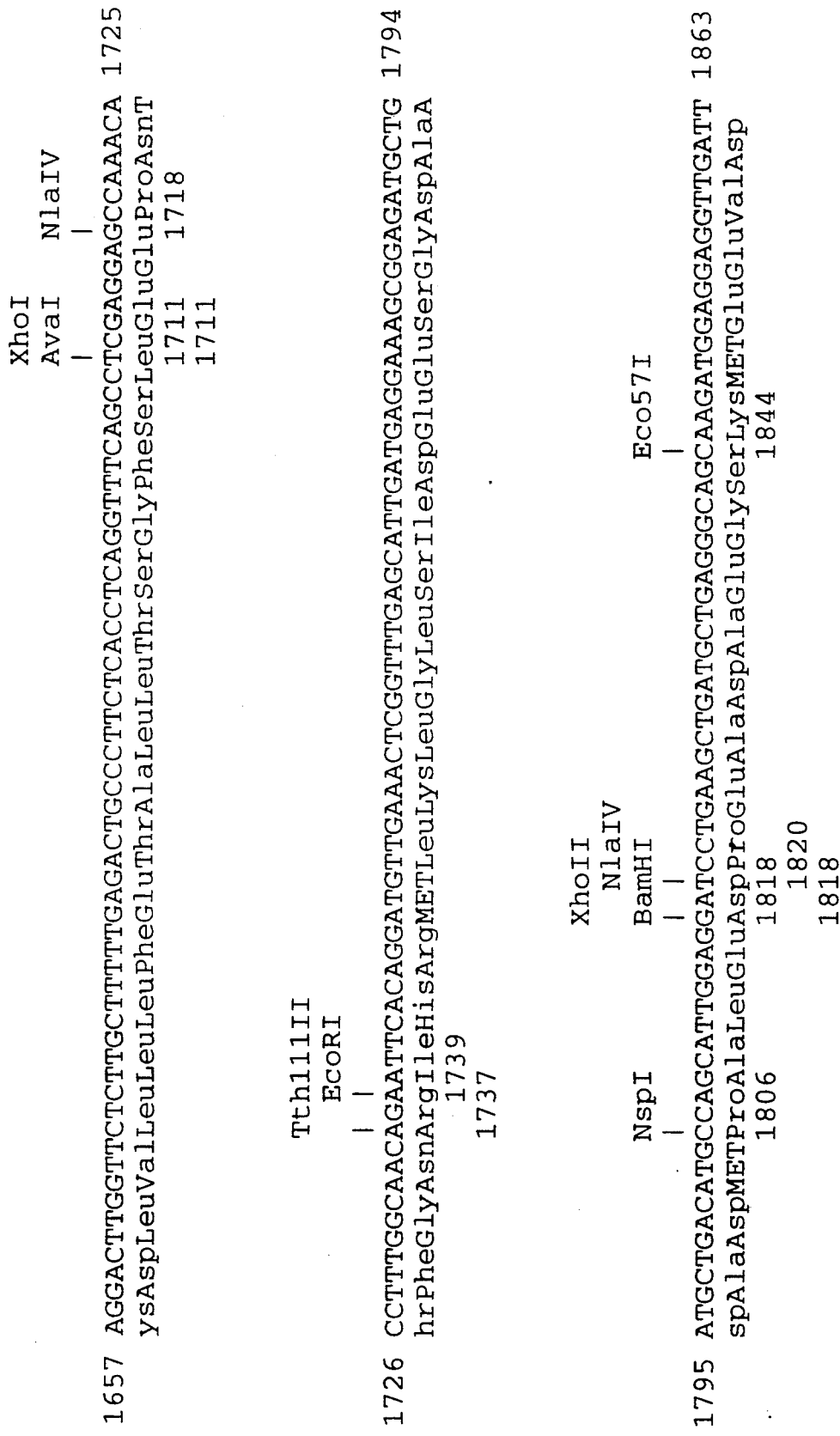
FIG. 1 shows the amino acid sequence and corresponding cDNA sequence of tomato hsp80A, clone 7115.

The 5' terminal portion, carried on a 223 bp KpnI-HindIII fragment, of cDNA clone 7100 was used to rescreen the cDNA library in the manner described above in order to isolate a longer cDNA clone. The longest clone isolated in this manner, referred to as 7115, is 1.9kb in length. Comparison of the predicted transcript size from 7115 and the 2.3 kb transcript revealed by Northern analysis, in addition to alignment of the predicted amino acid sequence from 7115 with yeast and fruit fly hsp80 amino acid sequences indicate that 7115 is not a full length cDNA clone; part of the 5' end is missing. DNA sequence of 7115 is shown in FIG. 1.

EXAMPLE 2

Isolation of HSP80 Genomic Clones

A Lambda Charon35 tomato genomic DNA library (Robert Fisher, UC Berkeley) was screened with 7100 cDNA, and several clones are isolated. One of these clones, Ghsp4, was sequenced by methods described above. Two introns one 995 bp in length and the other 109 bp in length, are found in genomic clone Ghsp4. FIG. 2. To determine whether any intron exists in the region covered by cDNAs 7100 and 7115, pairs of primers are used to amplify portions of the genomic sequence by employing the PCR reaction. Comparison to corresponding PCR reactions from the cDNA indicate that the regions represented by the cDNA 7100 do not contain introns, as the PCR products using the cDNAs as template are identical in size to PCR products using genomic DNA as template. However, subsequent DNA sequencing indicated that the extreme 5' end of cDNA clone 7115 does encompass the end of exon II.

To identify the transcription initiation point, dideoxynucleotide sequencing of plasmids and shoot tip mRNA as described by Geliebter, Focus (1987) 9:1; 2) and primer extensions of mRNA may be used. The primer extension assay is a modified version of McKnight (Cell (1981) 25:385-398). A primer near the 5' end of the known sequence is annealed to RNA (20 μg total RNA or 1-2 μg mRNA) in 10 μl annealing buffer (5X=1.25M KCl, 50 mM TRIS, pH8.3, 1 mM vanadyl) by heating to 80° C. for 10 minutes then incubatng at 65° C. for 1-2 hours. Next, 45 μl primer extension mix (10 mM MgCl2, 1-2 hours. Next, 45 μl primer extension mix (10 mM MgCL2, 5 mMDTT, 20 mM TRIS, pH8.3, 1 mM dNTPs, 100 μg/ml actinomycin D, and 1 mM vanadyl), and 30 units AMV-reverse transcriptase (Life Science Laboratories; Luton, England) are added to the annealing reaction. Extension of the primer proceeds at 50° C. for 1 hour. This reaction is then precipitated in EtOH, resuspended in a small volume of Sequenase stop buffer (U.S. Biochemical, Cleveland, OH), denatured, and loaded on a 6% polyacrylamide, 7M urea sequencing gel next to dideoxynucleotide sequencing reactions. The mRNA start site is mapped to about 70 bp upstream of the start codon. A sequence fitting the TATA box region concensus sequence is located 25 bp upstream of the transcriptional start site, and it is preceded by a fair match to the heat shock element consensus sequence (Pelham, Cell (1982) 30:517-528 and amin, et al. Mol. Cel. Biol. (1988) 8:3761-3769).

EXAMPLE 3

Southern Analysis

Southern analysis is performed using clone 7100 as a probe. Tomato genomic DNA isolated according to Dellaporta, et al. (Plant Mol. Bio. Reporter (1983) 1:19-21. The genomic DNA is digested with AsP718, BamHI, BglII and HindIII separately, and 10 μg/lane of digested DNA is electrophoresed on an agarose gel. The DNA is then transferred to a Zetaprobe nylon membrane according to procedures recommended by the manufacturer (Gibco-BRL; Grand Island, NY). The membrane is probed with 32P-labeled 7100 cDNA. Results show two bands with the intensity expected from a single copy gene. One of the bands appears to have imperfect homology to the probe. To determine if there are two loci, a Lambda Charon35 tomato genomic DNA library (described above) is probed with 7100 cDNA (described above), and several clones hybridize. By restriction digestion and Southern analysis, the clones characterized fall into two classes, A and B, corresponding to the two hybridization signals of the genomic Southern. Class A clones carry the Asp718 0.8kb fragment, while class B carry the hsp718 2.2kb fragment. DNA sequencing of subcloned regions from both types of clones confirm that two homologous loci exist. These loci were named hsp80-A and hsp80-B. Partial DNA sequence of an hsp80-B clone, Ghsp-7, is shown in FIG. 4. The A locus corresponds to the original 7100 cDNA clone.

The coding region of Ghsp4 is sequenced, as are the bordering 5' and 3' non-coding regions. All sequences are confirmed by sequencing in both directions. The structure of the A locus is shown in FIG. 2. The sequence shows a highly charged region composed essentially of basic and acidic residues between amino acid 210 and 270. FIG. 3 shows the amino acid sequence with the conserved residues. A sequence fitting the TATA box region concensus is located 25 bp upstream transcriptional start site, and it is preceded by a fair match to the heat shock element consensus sequence (Pelham, Cell (1982) 30:517-528 and Amin, et al., Mol. Cel. Biol. (1988) 8:3761-3769).

EXAMPLE 4

Determination of HSP80 Expression Pattern

To determine the expression pattern of hsp80 and the contribution of the A locus, two probes are employed a coding region probe, and a 3' region probe. The latter is specific to the A locus since it only hybridizes to one band on a genomic Southern and does not hybridize to genomic clones of the B locus. Northern analysis of RNA isolated from different plant organs reveals that A-locus-specific mRNA is very abundant in all developing tissues: root and shoot apices, flower meristem and early developing fruit. In these organs it represents about 1% of the total mRNA. The abundance of HSP80 message in meristems is at least ten times greater than in leaves.

Heat shock has little to moderate effect on hsp80 expression in shoot apices, as it appeared to increase it by 50% at the most. However, heat shock increases expression at least three fold in mature leaves. To test the effects of heat shock, 2-3 week old tomato plants in flats grown in a growth chamber are drenched with water and placed in a chamber with no forced air at 55° C. or 42° C. for one to two hours. Leaves and shoot tips are harvested, and RNA is extracted and subjected to Northern analysis as described in Example, 1. Control samples are not exposed to heat shock.

To test whether heavy metal induced hsp80 expression, excised leaves are floated on buffers containing cadmium salts. All treatments, including regular temperature and no salts, result in equal induction, indicating that leaf excision is sufficient to induce hsp80.

Northern blot analysis indicates that the A locus is a major contributor to the expression of hsp80 sine the A specific probe and the coding region probe give a similar pattern of hybridization. The B locus may be expressed with the same pattern as A, or may not be expressed at all in the tissues tested. Preliminary data suggest that the B locus may contribute about 50% of the hsp80 mRNA.

In situ hybridization

Root tips from one and one-half week old tomato seedlings are fixed in a 4% paraformaldehyde/phosphate buffered salne (PBS)/5mM MgC12 solution, pH 7.4 (PBS is 10 mM pH 7.4 phosphate buffer, made to 150 mM NaCl) (Singer, et al., Biotechniques (1986 4:230-250). Tissue is fixed overnight. After fixation, the tissues passed through a graded tertiary butyl alcohol (TBA) series starting at 50% TBA, infiltrated with Paraplast and cast into paraffin blocks for sectioning, (Berlyn and Miksche (1976) Botanical Microtechnique and Cytochemistry, State University Press, Ames, Iowa). Embedded root tips are sectioned longitudinally on a Reichert Histostat rotary microtome at 4 $\mu$M to achieve a one-cell layer thickness. Paraffin ribbons holding 7-10 root tip sections are affixed to gelatin-chrom alum subbed slides (Berlyn and Miksche (1976, supra) and held in a dust-free box until in situ hybridizations are performed. Slides ready to be hybridized are deparaffinized in xylene and rehydrated by passing through an ethanol hydration series as described in Singer, et al., Biotechniques (1986) 4:230-250.

An 2X hybridization mix is made consisting of 100 $\mu$l 20X SSC, 20 $\mu$l 10% BSA, 100 $\mu$l 750mM DTT, 200 $\mu$l 50% dextran sulfate, 50 $\mu$l RNasin, and 30 $\mu$l sterile water. 2.5 $\mu$l tRNA (20 mg/ml), 2.5 $\mu$l salmon sperm DNA (10 mg per ml) and $4 \times 10^6$ cpm probe were dried down on a lyophilizer. This mix is then resuspended in 25 $\mu$l 90° C. formamide and 25 $\mu$l 2× hybridization mix per slide. 40 $\mu$l of this hybridization mix was placed on each slide. A cover slip was placed over the sections and edges sealed with rubber cement. Slides were placed in slide holders inside a glass slide box, covered, and placed in a 37° C. dry oven overnight to hybridize. Posthybridization treatments are as described in Singer, et al., (1986), supra.

Autoradiography is performed as described in Kodak Materials for Light Microscope (1986) (available from Kodak), using Kodak liquid emulsion NTB-3. Slides are exposed in a light box for approximately two weeks. After developing the autoradiographic slides, root sections are stained in 0.05% toluidine blue and then dehydrated through a graded alcohol series: xylene: 100% ethanol, 1:1, followed by 2 changes 100% xylene. Slides are left for five minutes in each solution. Coverslips are mounted with cytoseal (VWR) and left on a slide warmer until dry (45- 50° C., 1-2 days.) Autoradiographic slides are then ready for microscopic examination and photomicrography.

In situ analysis of hsp80 expression provides information on the gene histological expression pattern. Strong expression is detected in root apices in the apical 5 mm region, especially in the region undergoing cell division and elongation. Expression is very low in mature root zone except in the cambial region. Apical shoots have a high level of hybridization in the apical meristem, residual and ground meristem Regions having higher hybridization levels are seen within meristems: they could be artifacts or may correspond to localized regions of higher cellular activity. In flower meristems, these regions of higher activity appear to be the regions of sympodial growth.

EXAMPLE 5

Construction of the HSP80A Expression Cassette

A genomic clone, Ghsp4 (isolated as described in Example 2 above), containing the hsp80A locus is digested with EcoRI and the resulting fragments are cloned into pUC18 to give the plasmid pCGN7117. A 2.1 kb fragment, extending from an EcoRI site at −2070 (relative to the start of transcription) to a 8gIII site at +60 is cloned into the BamHI/EcoRI sites of pBluescriptII SK(−) (Stratagene; La Jolla, CA) to give plasmid pCGN7123. The hsp80 5' region may be excised as an Asp718/SpeI fragment and cloned into the Asp718/XbaI sites of pCGN7398 (see below) to give plasmid pCGN7127. pCGN7398 contains the gusA locus (previously know as uidA, Jefferson, et al., EMBO J. (1987) 6:3901-3907) and the 3' region of the mannopine synthetase locus (mas, nucleotide 19,239 to 18,474; Barker et al, Plant Mol. Bio. (1983) 2:335-350. A polylinker containing Asp718 and XbaI is located 5' of the gusA-mas3' region. The hsp80 5' regions is cloned into the polylinker such that a chimeric gene is created in which transcription will initiate in the hsp80 5' region, continue through the gusA coding region, and terminate in the mas 3'. This chimeric gene is flanked by XhoI sites. These XhoI sites are then converted to PstI sites by cloning the XhoI fragment from pCGN7127, which carries the chimeric gene, into converter plasmid pCGN7328 (see below) resulting in the plasmid pCGN7128. pCGN7128 is digested with PstI, and the fragment carrying the chimeric gene is cloned into PstI-digested pCGN1547 (described below) to create the binary vector pCGN7129.

Construction of oCGN7398 pCGN7000 (see below) is digested with 8amHI and PstI. The 2.7kb fragment carrying the gus gene and the mas3' region is cloned into the BamHI/PstI sites of pCGN7300 (described below), resulting in plasmid "5-90-12". "5-90-12" is digested with XhoI and the the double 35S-gus-mas3' region is ligated with XhoI-digested pCGN1003 (described below), resulting in plasmid pCGN7304. pCGN7304 is digested with XhoI and BamHI to delete the 1.2 kb double 35S region. This region is replaced with a single 35S region, carried on an XbaI/BamHI fragment obtained from pCGN639 (described below). The resulting plasmid, carrying the single 35S-gus-mas3' region, is called "8-46A-1". The SmaI sited of "8-46A-1" is replaced with an XbaI site by ligating SmaI digested "8-46A-1" with XbaI linker DNA, resulting in the plasmid "9-47-19". The 35S region is deleted from "9-47 XbaI fragment, and is replaced with a polylinker containing unique restriction sites for PstI, SphI, NotI, KpnI, BglII, HindII, SmaI, SalI and XbaI, resulting in pCGN7398. pCGN7398 contains gus-mas3', with multiple cloning sites in front of gus.

pCGN7000 pCGN7000 is prepared from 8amHI/SacI digested pCGN1052 and pBI221.1 (Jefferson, R.S., Plant Mol. Bio. Rep. (1987) 5:387-405). The BamHI/SacI fragment containing the beta glucuronidase gene is excised from pBI221.1 and inserted into pCGN1052, resulting in pCGN7000. PCGN1052 (see below) is an expression plasmid containing the 5' and the 3' regions of the mas gene, separated by a polylinker, 5'TCTAGAG-GATCCCGGGTACCGAGCTCGAATTC3'.

pCGN1052

The 5.4 kb EcoRI fragment is removed from pVK232 (Knauf and Nester, Plasmid (1982) 8:45), by EcoRI digestion and cloned into EcoRI-digested pACYC184 (Chang and Cohen, J. Bacteriol. (1978) 134:1141-1156) to create pCGN14. The 1434 bp ClaI/SphI fragment of pCGN14, containing the mas 5' region (bp 20128-21562 according to the numbering of Barker et al., (Plant Mol. Biol. (1983) 2:335-350)) is cloned into AccI/SphI digested pUC19 (Yanisch-Perron, et al., Gene (1985) 33:103-119) to generate pCGN40. A 746 bp EcoRV-/NaeI fragment of the mas 5' region is replaced by an XhoI site by digesting pCGN40 with EcoRV and NaeI followed by ligation in the presence of a synthetic XhoI linker DNA to create pCGN1036. The 765 bp SstI/HindIII fragment (bp 18474-19239) of pCGN14, containing the mas 3' region, is cloned into SstI/HindIII digested pUC18 (Norrander, et al., Gene (1983) 26:101-106) to yield pCGN43. The HindIII site of pCGN43 is replaced with an EcoRI site by digestion with HindIII, blunt ending with Klenow enzyme, and ligation of synthetic EccRI linker DNA to create pCGN1034. The 767 bp EcoRI fragment of pCGN1034 is clone into EccRI-digested pCGN1036 in the orientation that places bp 19239 of the mas 3' region proximal to the mas 5' region to create pCGN1040. pCGN1040 is subjected to partial digestion with SstI, treated with T4 DNA polymerase to create blunt ends, and ligated in the presence of synthetic XhoI linker DNA; a clone is selected in which only the SstI site at the junction of bp 18474 and vector DNA (constructed in pCGN43 and carried into pCGN1040) is replaced by an XhoI site to generate pCGN1047.

pCGN565 (see below) is digested with EcoRI and HindIII, treated with Klenow enzyme to create blunt ends, and ligated in the presence of synthetic XhoI linker DNA to create pCGN1003; this recreates the EcoRI site adjacent to the XhoI linker. pCGN1003 is digested with EcoRI, treated with Klenow enzyme to create blunt ends, and ligated in the presence of synthetic PstI linker DNA to create pCGN1007. The 1.5 kb XhoI fragment of pCGN1047, containing the mas5' region and the mas3' region with multiple cloning sites between, is cloned into XhoI digested pCGN1007 to construct pCGN1052.

pCGN7300 pCGN7300 is constructed by digesting pCGN2113 (see below) with HindIII nd SalI. The cohesive ends are blunted by mung bean nuclease, and XhoI linkers 5'CCTCGAGG3' are inserted into the blunt ends to create an XhoI site.

pCGN2113 pCGN2113 contains a double-35S promoter and the tml-3' region with multiple cloning sites between them, contained in a pUC-derived plasmid backbone bearing an ampicillin resistance gene; the 35S/tml cassette is bordered by multiple restriction sites for easy removal. The plasmid pCGN2113 has been deposited with ATCC (Rockville, MD), accession number 40587, dated Mar. 2, 1989.

pCGN1003 pCGN565 (a cloning vector based upon pUC12 but containing pUC18 linkers) is digested with EcoRI and HindIII, treated with Klenow enzyme to create blunt ends, and ligated in the presence of synthetic XhoI linker DNA to create pCGN1003.

pCGN639 pCGN164 (see below) is digested with EcoRV and BamHI to release an EcoRV/8amHI fragment which contains a portion of the 35S promoter (bp 7340-7433); pCGN638 (see below) is digested with HindIII and EcoRV to release a HindIII/EcoRV fragment containing a different portion of the 35S promoter (bp 6493-7340). These two fragments are ligated into pCGN986 (see below) which has been digested with HindIII and BamHI to remove the HindIII/8amHI fragment containing the 35S promoter; this ligation produces pCGN639, which contains the backbone and tml-3' region from pCGN986 and the two 35S promoter fragments from pCGN164 and pCGN638.

pCGN164

The AluI fragment of CaMV (bp 7144–7735) (Gardner, et al., Nucl. Acids Res. (1981) 9:2871–2888) is cloned into the HincII site of M13mp7 (Vieira et al., Gene (1982) 19:259) to create C614. An EcoRI digest of C614 produces the EcoRI fragment from C614 containing the 35S promoter which is cloned into the EcoRI site of pUC8 (Vieira et al., (1982) ibid) to produce pCGN146. To trim the promoter region, the BglII site (bp7670) is treated with BglII and Bal31 and subsequently a BglII linker is attached to the Bal31 treated DNA to produce pCGN147. pCGN147 is digested with EcoRI and HphI and the resulting EcoRI/HphI fragment containing the 35S promoter is ligated into EcoRI/SmaI digested M13mp8 to create pCGN164.

pCGN638

Digestion of CaMV10 (Gardner et al., (1981) supra) with BglII produces a BglII fragment containing a 35S promoter region (bp 6493–7670) which is ligated into the BamHI site of pUC19 (Norrander et al., Gene (1983) 26:101–106) to create pCGN638.

Construction of oCGN7328 pCGN7328 is generated by digesting pUC19 with HindIII and EcoRI and ligating in a polylinker containing HindIII/BglII/PstI/XhoI/PstI/BglII/EcoRI.

Construction of pCGN1547 pCGN1547 (McBride and Summerfelt, Plant Mol. Biology (1990) 14(27):(269–276) is a binary plant transformation vector containing the left and right T-DNA borders of Agrobacterium tumefacIens octopine Ti-plasmid pTiA6 (Currier and Nester, J. Bact. (1976) 126:157–165), the gentamicin resistance gene of pPhlJI (Hirsch and Beringer, Plasmid (1984) 9:2871–2890), an Agrobacterium rhizogenes Ri plasmid origin of replication from pLJbBll (Jouanin et al., Mol. Gen. Genet. (1985) 201:370–374), the mas promoter region and mas 3′ region of pTiA6 with the kanamycin resistance gene of Tn5 (Jorgensen et al., Mol. Gen. Genet. (1979) 177:65), a ColEI origin of replication from pBR322 (Bolivar et al., Gene (1971) 2:95–133), and a IacZ′ screenable marker gene from pUC18 (Norrander et al., (1983) supra).

There are three major intermediate constructs used to generate pCGN1547:

pCGN1532 (see below) is made up of the pCGN1547 backbone, the pRi plasmid origin of replication, and the ColEI origin of replication.

pCGN1536 (see below) contains the mas5′-kan-mas3′ plant selectable marker region.

pCGN1541b contains the right and left T-DNA borders of the A.tumefacIens octopine Ti-plasmid, and the IacZ′ region, with multiple cloning sites (to use as a screenable marker in bacteria), from pUC19 (Yanisch-Perron et al., Gene (1985) 33:103–119). The construction of this plasmid is described below.

To construct pCGN1547 from the above plasmids, pCGNI536 is digested with XhoI, and the fragment containing the mas5′-kan-mas3′ ′ region is cloned into the XhoI site of pCGN1541b to give the plasmid pCGN1543, which contains T-DNA left border-mas5′-kan-mas3′-IacZ′-T-DNA right border. pCGN1543 is digested with BglII, and the fragment containing the T-DNA left border-mas5′-kan-mas3′-IacZ′-right border region is ligated into BamHI-digested pCGN1532 to give the complete binary vector.

pCGN1532

The 3.5 kb EcoRI-PstI fragment containing the gentamycin resistance gene is removed from pPhlJI (Hirsch and Beringer, Plasmid (1984) 12:139–141) by EcoRI-PstI digestion and cloned into EcoRI-PstI digested pUC9 (Vieira and Messing, Gene (1982) 19:259–268) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., Gene (1977) 2:95–113) to create pBR322Gm. pBR322Gm is digested with DraI and SphI, treated with Klenow enzyme to create blunt ends, and the 2.8 kb fragment cloned into the Ri origin-containing plasmid pLJbBll (Jouanin et al., Mol. Gen. Genet. (1985) 201:370–374) which has been digested with ApaI and made blunt-ended with Klenow enzyme, creating pLHbBIIGm. The extra ColEI origin and the kanamycin resistance gene are deleted from pLHbBIIGm by digestion with BamHI followed by self closure to create pGmBll. The HindIII site of pGmBII is deleted by HindIII digestion followed by treatment with Klenow enzyme and self closure, creating pGmBll-H. The PstI site of pGmBll-H is deleted by PstI digestion followed by treatment with Klenow enzyme and self-closure, creating pCGN1532.

pCGN1536

The 5.4 kb EcoRI fragment is removed from pVK232 (Knauf and Nester, Plasmid (1982) 8:45), by EcoRI digestion and cloned into EcoRI digested pACYC184 (Chang and Cohen, J. Bacteriol. (1978) 134:1141–1156) to create pCGN14. The 1434 bp ClaI-SphI fragment of pCGN14, containing the mas 5′region (bp20128–21562 according to numbering of Barker et al., Plant Mo. Biol. (1983) 2:335–350) is cloned into AccI-SphI digested pUC19 (Yanisch-Perron et al., (1985) supra) to generate pCGN40. A 746bp EcoRV-NaeI fragment of the mas 5′ region is replaced by an XhoI site by digesting pCGN40 with EcoRV and NaeI followed by ligation in the presence of a synthetic XhoI linker DNA to create pCGN1036. The 765 bp SstI-HindIII fragment (bp 18474–19239) of pCGN14, containing the mas 3′ region, is cloned into SstI-HindIII digested pUC18 (Norrander et al., (1983) supra) yield pCGN43. The HindIII site of pCGN43 is replaced with an EcoRI site by digestion with HindIII, blunt ending with Klenow enzyme, and ligation of synthetic EcoRI linker DNA to create pCGN1034. The 767 bp EcoRI fragment of pCGNI034 is cloned into EcoRI-digested pCGN1036 in the orientation that places bp 19239 of the mas 3′ region proximal to the mas 5′ region to create pCGN1040. pCGN1040 is subjected to partial digestion with SstI, treated with T4 DNA polymerase to create blunt ends, and ligated in the presence of synthetic XhoI linker DNA. A clone is selected in which only the SstI site at the junction of bp 18474 and vector DNA (constructed in pCGN43 and carried into pCGN1040) is replaced by an XhoI site to generate pCGN1047.

pCGN565 (see above) is digested with EcoRI and HindIII, treated with Klenow enzyme to create blunt ends, and ligated in the presence of synthetic XhoI linker DNA to create pCGN1003. This recreates the EcoRI site adjacent to the XhoI linker. pCGN1003 is digested with EcoRI, treated with Klenow enzyme to create blunt ends, and ligated in the presence of synthetic PstI linker DNA to create pCGN1007. The 1.5kb XhoI fragment of pCGN1047, containing the mas 5' region and the mas 3' region with multiple cloning sites between, is cloned into XhoI digested pCGN1007 to construct pCGN1052. A portion of the multiple cloning site of pCGN1052 is deleted by digestion with XbaI and SstI, treated with Klenow enzyme to make blunt ends, and ligated to generate pCGN1052ΔXS.

The 1 kb EcoRI-SmaI fragment of pCGN783 (pCGN783 is a binary plasmid containing the left and right T-DNA borders of A. tumefaciens (Barker et al., Plant Mol. Biol. (1983) 2:335-350). The gentamicin resistance gene of pPHIJI (Hirsch et al., Plasmid (1984), 9:2871-2890), the kanamycin resistance gene of Tn5 (Jorgenson et al, Mol. Gen. Genet. (1979) 177:65 and Wolff et al., Nucleic Aciods Research (1985) 13:355-367) and the 3' region from transcript 7 of pTiA6 (Barker et al., supra (1983). The plasmid pCGN783, has been deposited with ATCC (Rockville, MD), accession number 67868, dated Dec. 23, 1988.), containing the 1 ATG-kanamycin resistance gene, is cloned into EcoRI-SmaI digested Bluescript M13-KS (Stratagene; La Jolla, CA) to create pBSKm; this plasmid contains an M13 region allowing generation of single stranded DNA. Single stranded DNA is generated according to the supplier's recommendations, and in vitro mutagenesis is performed (Adelman et al., DNA (1983) 2:183-193) using a synthetic oligonucleotide with the sequence 5'GAACTCCAGGACGAGGC3' to alter a PstI site with the kanamycin resistance gene and make it undigestable, creating pCGN1534. pCGN1534 is digested with SmaI and ligated in the presence of synthetic EcoRI linker DNA to generate pCGN1535.

The 1 kb EcoRI fragment of pCGN1535 is cloned into EcoRI digested pCGN1052ΔXS to create the mas5'-kan mas3' plant selectable marker cassette pCGN1536.

pCGN1541b pCGN565RBa2X (see below) is digested with 8gIII and XhoI, and the 728 bp fragment containing the T-DNA right border piece and the lacZ' gene is ligated with BglII-XhoI digested pCGN65DKX-S+K (see below), replacing the BglII-oI right border fragment of pCGN65DKX-S+K. The resulting plasmid, pCGN65a2X contains both T-DNA borders and the lacZ' gene. The ClaI fragment of pCGN65 Δ2X is replaced with an XhoI site by digesting with ClaI, blunting the ends using the Klenow fragment, and ligating with XhoI linker DNA, resulting in plasmid pCGN65 α2XX. pCGN65 Δ2XX is digested with 8gIII and EcoRV, treated with the Klenow fragment of DNA polymerase I to create blunt ends, and ligated in the presence of BglII linker DNA, resulting in pCGN65 α2XX'. pCGN65 α2XX' is digested with BglII and ligated with BglII digested pCGN1538 (see below), resulting in pCGN1541a, which contains both plasmid backbones. pCGN1541a is digested with XhoI and religated. Ampicillin resistant, chloramphenicol sensitive clones are chosen, which lack the pACYC184-derived backbone, creating pCGN1541b.

pCGN1538 is generated by digesting pBR322 with EcoRI and PvuII, treating with Klenow to generate blunt ends, and ligating with BglII linkers. pCGN1538 is ampicillin resistant, tetracycline sensitive.

pCGN65ΔKX-S+K pCGN501 is constructed by cloning a 1.85 kb EcoRI-XhoI fragment of pTiA6 (Currier and Nester, J. Bact. (1976) 126:157-165) containing bases 13362-15208 (Barker et al., Plant Mo. Biol. (1983) 2:335-350) of the T-DNA (right border), into EcoRI-SalI digested M13mp9 (Vieira and Messing, Gene (1982) 19:259-268). pCGN502 is constructed by cloning a 1.6 kb HindIII-SmaI fragment of pTiA6, containing bases 602-2212 of the T-DNA (left border), into HindIII-SmaI digested M13mp9. pCGN501 and pCGN502 are both digested with EcoRI and HindIII and both T-DNA-containing fragments cloned together into HindIII digested pUC9 (Vieira and Messing, Gene (1982) 19:259-268) to yield pCGN503, containing both T-DNA border fragments. pCGN503 is digested with HindIII and EcoRI and the two resulting IndIII-EcoRI fragments (containing the T-DNA borders) are cloned into EcoRI digested pHC79 (Hohn and Collins, Gene (1980) 11:291-298) to generate pCGN518. The 1.6kb KpnI-EcoRI fragment from pCGN518, containing the left T-DNA border, is cloned into KpnI-EcoRI digested pCGN565 to generate pCGN580. The BamHI-BglII fragment of pCGN580 is cloned into the BamHI site of pACYC184 (Chang and Cohen, J. Bacteriol. (1978) 134:1141-1156) to create pCGN51. The 1.4 kb BamHI-SphI fragment of pCGN60 (see pCGN56560 2X description below) containing the T-DNA right border fragment, is cloned into BamHI-SphI digested pCGN51 to create pCGN65, which contains the right and left T-DNA borders.

pCGN65 is digested with KhnI and XbaI, treated with Klenow enzyme to create blunt ends, and ligated in the presence of synthetic BglII linker DNA to create pCGN6566 KX. pCGN65ΔKX is digested with SalI, treated with Klenow enzyme to create blunt ends, and ligated in the presence of synthetic XhoI linker DNA to create pCGN65ΔKX-S+X.

pCGN565RBa2X pCGN451 (see below) is digested with HpaI and ligated in the presence of synthetic SphI linker DNA to generate pCGN55. The XhoI-SphI fragment of pCGN55 (bp13800-15208, including the right border, of Agrobacterium tumefaciens T-DNA; (Barker et al., Gene (1977) 2:95-113) is cloned into SalI-SphI digested pUC19 (Yanisch-Perron et al., (1985) supra) to create pCGN60. The 1.4 kb HindIII-8amHI fragment of pCGN60 is cloned into HindIII-BamHI digested pSP64 (Promega, Inc.) to generate pCGN1039. pCGN1039 is digested with SmaI and NruI (deleting bp14273-15208; (Barker et al., Gene (1977) 2:95-113) and ligated in the presence of synthetic BglII linker DNA, creating pCGN1039ΔNS. The 0.47 kb EcoRI-HindIII fragment of pCGNI039ΔNS is cloned into EcoRI-HindIII digested pCGN565 to create pCGN565RB. The HindIII site of pCGN565RB is replaced with an XhoI site by digesting with HindIII, treating with Klenow enzyme, and ligating in the presence of synthetia XhoI linker DNA to create pCGN565RB-H+X.

pUC18 (Norrander et al., Gene (1983) supra) is digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme in such a orientation that the lacZ' promoter is proximal to the right border fragment. This construct, pCGN565RBa2x is positive for lacZ' expression when plated on an appropriate host and contains bp 13990-14273 of the right border fragment (Barker et al., Plant Mb. Biol. (1983) 2:335-350) having deleted the AccI-SphI fragment (bp 13800-13990).

pCGN451 pCGN451 contains an ocs5'-ocs3' cassette, including the T-DNA right border, cloned into a derivative of pUC8 (Vieira and Messing, supra). The modified vector is derived by digesting pUC8 with HIncII and ligating in the presence of synthetic linker DNA, creating pCGN416, and then deleting the EcoRI site of pCGN416 by EcoRI digestion followed by treatment with Klenow enzyme and self-ligation to create pCGN426.

The ocs5'-ocs3' cassette is created by a series of steps from DNA derived from the octopine Ti-plasmid pTiA6 (Currier and Nester, supra). To generate the 5' end, which includes the T-DNA right border, an EcoRI fragment of pTiA6 (bp 13362-16202 (the numbering is by Barker, et al., (Plant Mol. Bio (1983) 2:335-350) for the closely related Ti plasmid pTi15955)) is removed from pVK232 (Knauf and Nester, Plasmid (1982) 8:45) by EcoRI digestion and cloned into EcoRI digested pACYC184 (Chang and Cohen, supra) to generate pCGN15.

The 2.4kb BamHI-EcoRI fragment (bp 13774-16202) of pCGN15 is cloned into EcoRI-BamHI digested pBR322 (Bolivar, et al., supra) to yield pCGN429. The 412 bp EcoRI-BamHI fragment (bp 13362-13772) of pCGN15 is cloned into EcoRI-BamHI digested pBR322 to yield pCGN407. The cut-down promoter fragment is obtained by digesting pCGN407 with XmnI (bp 13512), followed by resection with Bal31 exonuclease, ligation of synthetic EcoRI linkers, and digestion with BamHI. Resulting fragments of approximately 130 bp are gel purified and cloned into M13mp9 (Vieira and Messing, supra) and sequenced. A clone, I-4, in which the EcoRI linker has been inserted at bp 1362 between the transcription initiation point and the translation initiation codon is identified by comparison with the sequence of de Greve, et al., (J. Mol. Appl. Genet. (1982) 1:499-512). The EcoRI cleavage site is at position 13639, downstream from the mRNA start site. The 141 bp EcoRI-BamHI fragment of I-4, containing the cut-down promoter, is cloned into EcoRI-8amHI digested pBR322 to create pCGN428. The 141 bp EcoRI-BamHI promoter piece from pCGN428, and the 2.5 kb EcoRI-BamHI ocs5' piece from pCGN429 are cloned together into EcoRI digested pUC19 (Yanisch-Perron (1985) supra) to generate pCGN442, reconstructing the ocs upstream region with a cut-down promoter section.

To generate the ocs3' end, the HindIII fragment of pLB41 (D. Figurski, UC San Diego) containing the gentamicin resistance gene is cloned into HindIII digested pACYC184 (Chang and Cohen, supra) to create pCGN413b. The 4.7 kb BamHI fragment of pTiA6 (supra), containing the ocs3' region, is cloned into BamHI digested pBR325 (F. Bolivar, Gene (1978) 4:121-136) to create 33c-19. The SmaI site at position 11207 (Barker, supra) of 33c-19 is converted to an XhoI site using a synthetic XhoI linker, generating pCGN401.2. The 3.8 kb 8amHI-EcoRI fragment of pCGN401.2 is cloned into 8amHI-EcoRI digested pCGN413b to create pCGN419.

The ocs5'-ocs3' cassette is generated by cloning the 2.64 kb EcoRI fragment of pCGN442, containing the 5' region, into EcoRI digested pCGN419 to create pCGN446. The 3.1 kb XhoI fragment of pCGN446, having the ocs5' region (bp 13639-15208) and ocs3' region (bp 11207-12823), is cloned into the XhoI site of pCGN426 to create pCGN451.

EXAMPLE 6

Generation of Transformed Plants

The binary vector, pCGN7129 is introduced into the Agrobacterium tumefaciens strain LBA4404 (Hoekema, et al., Nature (1983) 303:179-181) by transformation. Nicotiana tobacum var. "Xanthi nc" is cocultivated as described by Horsch, et al. (Science (1985) 227:1229-1231).

Tobacco leaf explants, roughly 5-10 mm by 5-10 mm, are cut from young leaves, approximately 3-5cm long and third to sixth from the apex of Nicotiana tobacum cv xanthi-nc which are grown under axenic conditions in solid medium: Murashige Minimal Organics (#1118 Gibco Laboratories, New York), 7% phytagar, 1mg/1 indole-3-acetic acid, 0.15mg/1 kinetin. The explants are plated on a sterile #1 Whatman filter paper (Whatman Ltd., Maidstone, England) which covers the surface of solid medium containing Murashige Minimal Organics, 6% phytagar, 40mg/1 adenine sulfate, 2mg/1 indole-3-acetic acid, 2mg/1 kinetin, and they are then incubated for 24 hours in the dark at 24° C.

The Agrobacterium are grown for 4-5 days on AB minimal medium (Watson, et al., J. Bacteriol. (1975) 123:255-264) containing 100 mg/1 gentamycin sulfate and 100 mg/1 streptomycin sulfate. Single colonies were inoculated into 5mls of MG/L broth (50% Luria broth and 50% mannitol-glutamate salts medium (Garfinkel and Nester, J.BacterIol. (1980) 144:732-743)) and are incubated overnight in a shaker at 30° C. and 180 rpm before co-cultivation.

Following the preincubation period, the explants are dipped into the bacterial suspension of $3.3 \times 10^8$ cells/ml for approximately 5 minutes, blotted on sterile paper towels and replated on the same plates. After 48 hours, the explants are placed on selection medium containing the same plate medium as above plus 350mg/1 cefotaxime and 100mg/1 kanamycin. The explants are transferred to fresh media every 2 weeks. At the 6th week transfer and thereafter, shoot and green callus are trimmed from explants and placed on solid media: Murashige Minimal Organics, .5mg/1 indole-3-acetic acid, 2 mg/1 kinetin, 40 mg/1 adenine sulfate, 350 mg/1 cefotaxime, 100 mg/1 kanamycin. Shoots are harvested beginning about 4 weeks after co-cultivation and placed in 50 ml culture tubes with 25 ml of solid medium (MS Minimal Organics, 7% bactagar, 1 mg/1 indole-3-butyric acid, 350 mg/1 cefotaxime, 100 mg/1 kanamycin). Shoots rooted in 1-2 weeks and are then transplanted into soil and placed in growth chambers. All in vitro tissue is grown at 24°-28° C., 12 hours light, 12 hours dark, light intensity 80-100 $\mu Em - ^2 S - ^1$.

To assure independent transformation events, only individuals from different callus clumps are rooted. Transformed plants generated by Agrobacterium cocultivation are potted in a soil mix and grown in a growth chamber, with 12 hour day periods, at 25° C. and 400 $\mu Em - ^2 s - ^1$.

EXAMPLE 7

Analysis of Transformed Plants

Tissue from normally growing leaves (1 to 3 cm), excised leaves, and wounded leaves is assayed for β-glucuronidase activity as described by Jefferson et al., (1987, supra). For wound induction studies, leaves are wounded by briefly closing large tweezers in several places on the leaf blade, without crushing the midrib. Gus activity is measured ninety minutes after wounding and compared to measurements taken at time zero. Normal leaves of individual transformed plants vary from showing very little activity to no detectable activity. Leaves excised and incubated for six hours show induction of gus activity whether or not heat shock is performed. Leaves that are wounded and left on the plant also show induction of gus activity.

To determine the expression in apical shoots, a section of the apical region is incubated with the histological substrate X-gluc. An intense blue precipitate is formed. This illustrates that the pattern of expression of trangenic plants reproduces the expression pattern of the endogenous gene.

EXAMPLE 8

Determination of Scaffold-Attached Regions

In this example, the presence of scaffold-attached regions, which are regions where DNA is attached to the nuclear scaffold, is determined.

Isolation of Nuclei

The method of Luthe and Quatrano (Plant Physiol. (1980) 65:305-308), modified by Gallagher and Ellis (EMBO (1982) 1:1493-1498) is used to isolate nuclei.

10 grams of tomato shoot tips are harvested from 3-week old plants as described in Example 1. The tissue is homogenized in 20 mls of solution A (440 mM sucrose, 25 mM TRIS-HCL pH7.6, 10 mM MgCl$_2$, 10mM BME, 2 mM spermine, 2.5% Ficoll F400, 5.0% Dextran 40,000MW, 0.5% triton X-100) using a polytron (Brinkman Instruments; Westbury, NY). The homogenized mixture is filtered through cheesecloth, followed by filtration through miracloth to remove debris. The filtrate is centrifuged at 2500 xg for 5 minutes. The pellet is resuspended in 3 mls solution B (same as solution A above without the spermine) and separated over a percoll step gradient with an 85% sucrose pad (4000xg for 30 minutes). The nuclei are collected and the volume is brought to 5 mls with solution B plus 5 μl RNAsin (40U/μl). This mixture is centrifuged at 1800 rpm (Beckman JS13 rotor) and the nuclei are removed and brought up to 5 mls with solution B plus 5 μl RNAsin (40U/μl). The centrifugation is repeated, and the nuclei removed and brought up in 5 mls of solution C (440 mM sucrose, 50 mM TRS-HCL,pH 7.8, 5 mM MgCl$_2$, 10mM BME, 20% glycerol (sterile)). This mixture is centrifuged at 1800 rpm in a Beckman JS13 rotor, and the nuclei are resuspended in 1 ml solution C. The mixture is stored in 100 μl aliquots at −70° C.

Extraction of Nuclear Scaffolds

The method of Bode and Maass (Biochem.(1988) 27:4706-4711) is used for extraction of the DNA which is bound to the nuclear scaffold.

A known amount of DNA of genomic clone 7117 is digested with XbaI, EcoRI, Asp718, SalI. FIG. 5. The bands are ranked by size. 1 μg of these fragments is end labeled with the Klenow fragment of DNA polymerase I according to the method of Maniatis (1982, supra). An aliquot of nuclei (see above) is analyzed to determine the number of nuclei contained therein. The aliquot is stained with approximately 1 ng of ehhidium bromide, and the nuclei are counted under UV light on a hemocytometer.

Nuclear scaffolds are isolated based to the method of Bode and Maass (Biochemistry (1988) 27:4706-4711). Nuclei are suspended in 100 82 1 freshly made nuclear buffer (5 mM Tris-HCL, pH 7.4, 0.05 mM spermine, 0.125 mM spermidine, 20mM KCl, 1% thiodiglycol, 0.1% digitonin, 0.2mM PhMeSo2F, and 0.1% aprotinin) and shaken gently at 37° C. for 20 minutes. After 20 minutes in nuclear buffer, 1.5 ml lithium 3,5-diiodosalicylate (LIS) buffer [25mM LIS, 20mM N-(2-hydroxyethyl-piperazine-N'-2-ethanesulfonic acid (Hepes)-NaOH, pH 7.4, 0.1 M lithium acetate, lmM EDTA, and 0.1% digitonin]is added, and the nuclear pellet is carefully homogenized. The suspension is kept on ice for 0.5-2 minutes and homogenized once more. After centrifugation (2400xg, 5 minutes, 4° C.), the pellet consists of nuclear halos which are transferred to a capped centrifugation tube containing 20 ml of sterile-filtered digestion buffer (20 mM Tris-HCl, pH 7.4, 0.05 mM spermine, 0.125 mM spermidine, 20mM KCL, 70mM NaCl, 10mM MgCl$_2$). The tube is gently rocked for 30 minutes at room temperature and centrifuged as before; this procedure is repeated at least twice. Halos are removed and subjected to restriction digestion with EcoRI.

Nuclear halos, pretreated for 3 hours with the above enzyme, are supplied with approximately 200,000 cpm of labeled clone 7117 fragments and with 20-140 μg of sonicated E. coli competitor DNA. Samples are then incubated, with gentle rocking, at 37° C. overnight. The mixture is centrifuged at 6000 rpm for 10 minutes, and the pellet is washed with 500 μl digestion buffer (see above) and centrifuged again. 100 μl of TES (10mM Tris-HCl, pH 8.5, 0.1 M EDTA, 1% SDS) is added to the supernatant, and 300 μl is added to the pellet. 100 μg of proteinase K is added to each, and both samples are heated at 60° C. for 2 hours. 600 μl of 0.6M LiCl (-20° C.) in EtOH is added to each and the mix is incubated on ice 1 hour. The samples are centrifuged, and the LiCl precipitation is repeated. The pellets are resuspended in water, and 10,000 cpm samples are loaded on a 4% acrylamide, 7M urea gel. After electorphoresis, the dried gel is exposed to X-ray film. The autoradiograph shows the following: Nine bands are present in the lane corresponding to the clone 7117 sample and all are clearly visible. The lane corresponding to the "supernatant" sample contains the same nine bands, all clearly visible. The lane corresponding to the "pellet" sample contains the nine bands as well. However, three of the bands are very faint relative to the signals seen in the supernatant lane, four bands are clearly lighter than the same bands in the supernatant lane, while two of the bands are very dark relative to the same bands in the supernatant lane. These results lead to the conclusion that the dark bands (blanks #2 and #3) correspond to DNA that was bound to the nuclear scaffold, thus giving evidence of scaffold-attachment regions. Band #8 was bound to the scaffold in one of two experiments. The sequence found in bands #2, 3 and 8 are shown in Table I below.

TABLE I

| Band | 2 | | 3 | | 8 | |
|---|---|---|---|---|---|---|
| T Boxes | TTATTTTTC | T Box | ATTTTTTTT | T Box | ATATTTTTT |
| | AAAAAAATTAA* | | | | | |
| A Boxes | TATAAATAAA | A Boxes | AATAAATAAA | | | |
| | AATAAATAAT | | AATCAAATAAA | | | |
| | AATAAAATAA | | AATTAAATAAA | | | |

Mismatches to Drosophila consensus are underlined
*opposite strand = TTAATTTTTTT (T Box)

The presence of these bands in the supernatant sample may be due to saturation of the system with DNA, resulting in a large DNA:nuclear scaffold ratio in which there was not enough scaffold to bind all the available DNA. Interestingly, the bands that bound strongly to the nuclease scaffold contained multiple scaffold binding sites and that these bands correspond to the promoter region of the tomato hsp80 (See FIG. 5).

From the above, the sequence and usefulness of the hsp80 transcription initiation region is demonstrated as well as the identification of the first plant nuclear scaffold regions.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A DNA construct comprising, in the 5' to 3' direction of transcription, a 5' non-coding region from a tomato hsp80 gene and (b) a DNA sequence of interest wherein said sequence is heterologous to said 5' non-coding region.

2. The DNA construct of claim 1 wherein said 5' non-coding region comprises from about nucleotide +60 to nucleotide −2070 of FIG. 1.

3. The DNA construct of claim 1 wherein said 5' non-coding region is free of the tomato hsp80 structural sequence.

4. The DNA construct of claim 1 wherein said 5' non-coding region comprises a transcriptional and translational initiation region.

5. The DNA construct of claim 4 further comprising a trnscriptional termination region functional in a plant cell.

6. The DNA construct of claim 5 wherein said transcriptional termination region is from a tomato hsp80 gene.

7. The DNA construct of claim 5 wherein said DNA sequence of interest is a structural gene.

8. The DNA construct of claim 1 wherein said DNA sequence of interest is in the anti-sense orientation.

9. The DNA construct of claim 8 wherein said DNA sequence of interest is anto-sense to a tomato hsp80 encoding sequence.

10. A transgenic plant cell comprising a DNA construct according to claim 1.

11. The transgenic plant cell of claim 10 further comprising a marker for the identification of transformed cells.

12. The transgenic plant cell of claim 10 wherein said plant cell is a solanaceous plant cell.

13. A plant comprising a transgenic plant cell according to claim 10.

14. A plant comprising a transgenic plant cell according to claim 11.

15. A solanaceous plant comprising a transgenic plant cell according to claim 12.

16. A method of providing for increased transcription of a DNA sequence of interest in solanaceous plant tissue following wounding, wherein said method comprises the steps of:

growing a solanaceous plant having integrated in its genome a DNA construct comprising, in the direction of transcription, (a) a 5' non-coding region from a tomato hsp80 gene, and (b) a DNA sequence of interest wherein said sequence is heterologous to said 5' non-coding region, and wherein transcription of said DNA sequence of interest is increased in said solanaceous plant tissue upon wounding.

17. A method of providing for increased transcription of a DNA sequence of interest in rapidly growing plant tissue as compared to mature plant tissue, wherein said method comprises the steps of:

growing a solanaceous plant having integrated in its genome a DNA construct comprising, in the direction of transcription, (a) 5' non-coding region from a tomato hsp80 gene, and (b) a DNA sequence of interest wherein said sequence is heterologous to said 5' non-coding region.

18. The method of claim 17 wherein said rapidly growing plant tissue is selected from the group consisting of meristem tissue, root apical tissue, shoot apical tissue and developing fruit tissue.

19. The method of claim 17 wherein said 5' non-coding region comprises a transcriptional and translational initiation region.

20. The method of claim 17 or 19 wherein said DNA construct further comprises a transcriptional termination region functional in a plant cell.

* * * * *